(12) United States Patent
Pate et al.

(10) Patent No.: US 9,891,165 B2
(45) Date of Patent: *Feb. 13, 2018

(54) CHIRPED PULSE FREQUENCY-DOMAIN COMB FOR SPECTROSCOPY

(71) Applicant: University of Virginia Patent Foundation, Charlottesville, VA (US)

(72) Inventors: Brooks Hart Pate, Charlottesville, VA (US); Kevin K. Lehmann, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,036

(22) Filed: Sep. 1, 2016

(65) Prior Publication Data

US 2017/0089831 A1   Mar. 30, 2017

Related U.S. Application Data

(63) Continuation of application No. 14/718,624, filed on May 21, 2015, now Pat. No. 9,442,079, which is a
(Continued)

(51) Int. Cl.
*G01J 3/30* (2006.01)
*G01N 21/3586* (2014.01)
(Continued)

(52) U.S. Cl.
CPC ......... *G01N 21/3586* (2013.01); *G01N 22/00* (2013.01); *G01J 3/44* (2013.01);
(Continued)

(58) Field of Classification Search
CPC ........ G01N 21/67; G01N 21/69; G01N 21/62; G01N 21/3103; G01J 3/443
See application file for complete search history.

(56) References Cited

U.S. PATENT DOCUMENTS 3,909,705 A   9/1975   Tschopp
4,464,570 A   8/1984   Allemann et al.
(Continued)

FOREIGN PATENT DOCUMENTS

CN   101512286 A   8/2009
CN   103583003 A   2/2014
(Continued)

OTHER PUBLICATIONS

U.S. Appl. No. 13/704,483, filed Feb. 27, 2013, Chirped Pulse Frequency-Domain Comb for Spectroscopy, Now U.S. Pat. No. 9,046,462.
(Continued)

*Primary Examiner* — Abdullahi Nur
(74) *Attorney, Agent, or Firm* — Schwegman Lundberg & Woessner, P.A.

(57) ABSTRACT

A pulse train comprising chirped pulses can be used to excite a sample, such as for spectroscopic analysis. The respective chirped pulses can include a frequency sweep to establish a first frequency-domain comb. A width of frequency-domain comb peaks can be established at least in part by a total duration of the pulse train, and a bandwidth of the first frequency-domain comb can be determined at least in part by a bandwidth of the frequency sweep of the respective chirped pulses. A free-space or enclosed sample interaction region can be used.

31 Claims, 15 Drawing Sheets

Related U.S. Application Data continuation of application No. 13/704,483, filed as application No. PCT/US2011/040876 on Jun. 17, 2011, now Pat. No. 9,046,462.

(60) Provisional application No. 61/355,862, filed on Jun. 17, 2010.

(51) Int. Cl.
```
G01N 22/00    (2006.01)
G01N 21/31    (2006.01)
G01N 21/62    (2006.01)
G01N 21/69    (2006.01)
G01J 3/44     (2006.01)
G01N 21/67    (2006.01)
```

(52) U.S. Cl.
CPC ............ *G01N 21/31* (2013.01); *G01N 21/62* (2013.01); *G01N 21/67* (2013.01); *G01N 21/69* (2013.01)

(56) References Cited

U.S. PATENT DOCUMENTS

| | | | |
|---|---|---|---|
| 4,967,160 A | 10/1990 | Quievy et al. | |
| 5,047,636 A | 9/1991 | Farrar et al. | |
| 5,508,661 A | 4/1996 | Keane et al. | |
| 8,748,822 B1 | 6/2014 | Gerecht et al. | |
| 8,873,043 B2 | 10/2014 | Pate et al. | |
| 9,046,462 B2 * | 6/2015 | Pate | G01N 21/3586 |
| 9,442,079 B2 * | 9/2016 | Pate | G01N 21/3586 |
| 9,482,577 B2 | 11/2016 | Pate et al. | |
| 2004/0007666 A1 | 1/2004 | Griffey et al. | |
| 2005/0058218 A1 | 3/2005 | Jenkins | |
| 2005/0168735 A1 | 8/2005 | Boppart et al. | |
| 2006/0049981 A1 | 3/2006 | Merkel et al. | |
| 2007/0223936 A1 | 9/2007 | Babbitt et al. | |
| 2008/0224908 A1 | 9/2008 | Li et al. | |
| 2008/0285606 A1 | 11/2008 | Kippenberg et al. | |
| 2009/0073432 A1 | 3/2009 | Jalali et al. | |
| 2009/0161092 A1 | 6/2009 | Zanni et al. | |
| 2010/0046003 A1 | 2/2010 | Le Floch et al. | |
| 2010/0290025 A1 | 11/2010 | Parker | |
| 2013/0154611 A1 | 6/2013 | Pate et al. | |
| 2013/0265573 A1 | 10/2013 | Pate et al. | |
| 2015/0253261 A1 | 9/2015 | Pate et al. | |
| 2015/0260575 A1 | 9/2015 | Pate et al. | |
| 2016/0131600 A1 | 5/2016 | Pate et al. | |
| 2017/0176256 A1 | 6/2017 | Pate et al. | |

FOREIGN PATENT DOCUMENTS

| | | |
|---|---|---|
| JP | 2016521859 A | 7/2016 |
| TW | 201510504 A | 3/2015 |
| WO | WO-2011160013 A1 | 12/2011 |
| WO | WO-2012129089 A1 | 9/2012 |
| WO | WO-2014201230 A1 | 12/2014 |

OTHER PUBLICATIONS

U.S. Appl. No. 14/718,624, filed May 21, 2015, Chirped Pulse Frequency-Domain Comb for Spectroscopy, Now U.S. Pat. No. 9,442,079.
U.S. Appl. No. 13/912,548, filed Jun. 7, 2013, Segmented Chirped-Pulse Fourier Transform Spectroscopy, Now U.S. Pat. No. 8,873,043.
U.S. Appl. No. 14/494,315, filed Sep. 23, 2014, Segmented Chirped-Pulse Fourier Transform Spectroscopy, Now U.S. Pat. No. 9,482,577.
U.S. Appl. No. 15/338,851, filed Oct. 31, 2016, Segmented Chirped-Pulse Fourier Transform Spectroscopy.
U.S. Appl. No. 14/898,077, filed Dec. 11, 2015, Apparatus and Techniques for Fourier Transform Millimeter-Wave Spectroscopy.
"U.S. Appl. No. 13/704,483, Notice of Allowance dated Feb. 3, 2015", 10 pgs.
"U.S. Appl. No. 13/704,483, Notice of Allowance dated Oct. 9, 2014", 11 pgs.
"U.S. Appl. No. 13/704,483, Preliminary Amendment dated Dec. 14, 2012", 8 pgs.
"U.S. Appl. No. 13/912,548, Notice of Allowance dated Mar. 18, 2014", 12 pgs.
"U.S. Appl. No. 13/912,548, Notice of Allowance dated Jul. 1, 2014", 9 pgs.
"U.S. Appl. No. 14/494,315, Final Office Action dated Dec. 31, 2015", 9 pgs.
"U.S. Appl. No. 14/494,315, Non Final Office Action dated Jul. 8, 2015", 6 pgs.
"U.S. Appl. No. 14/494,315, Notice of Allowance dated Jun. 29, 2016", 9 pgs.
"U.S. Appl. No. 14/494,315, Response filed May 3, 2016 to Final Office Action dated Dec. 31, 2015", 8 pgs.
"U.S. Appl. No. 14/494,315, Response filed Dec. 7, 2015 to Non Final Office Action dated Jul. 8, 2015", 9 pgs.
"U.S. Appl. No. 14/718,624, Final Office Action dated Dec. 30, 2015", 8 pgs.
"U.S. Appl. No. 14/718,624, Non Final Office Action dated Jul. 16, 2015", 6 pgs.
"U.S. Appl. No. 14/718,624, Notice of Allowance dated Apr. 4, 2016", 12 pgs.
"U.S. Appl. No. 14/718,624, Notice of Allowance dated May 10, 2016", 6 pgs.
"U.S. Appl. No. 14/718,624, Response filed Feb. 29, 2016 to Final Office Action dated Dec. 30, 2015", 11 pgs.
"U.S. Appl. No. 14/718,624, Response filed Oct. 16, 2015 to Non Final Office Action dated Jul. 16, 2015", 7 pgs.
"U.S. Appl. No. 14/898,077, Examiner Summary dated May 12, 2017", 1 pg.
"U.S. Appl. No. 14/898,077, Notice of Allowance dated May 30, 2017", 13 pgs.
"U.S. Appl. No. 15/338,851, Notice of Allowance dated May 2, 2017", 10 pgs.
"U.S. Appl. No. 15/338,851, Notice of Allowance dated Jun. 2, 2017", 10 pgs.
"U.S. Appl. No. 15/338,851, Preliminary Amendment filed Mar. 10, 2017", 72 pgs.
"Chinese Application Serial No. 201280023629.7, Office Action dated Feb. 1, 2016", w/English Translation, 16 pgs.
"European Application Serial No. 11796503.8, Communication pursuant to Article 94(3) EPC dated Aug. 3, 2016", 5 pgs.
"European Application Serial No. 11796503.8, Extended European Search Report dated Sep. 24, 2015", 8 pgs.
"European Application Serial No. 11796503.8, Response filed Apr. 25, 2016", 12 pgs.
"European Application Serial No. 11796503.8, Response filed Dec. 12, 2016 to Communication pursuant to Article 94(3) EPC dated Aug. 3, 2016", 11 pgs.
"European Application Serial No. 12761002.0, Extended European Search Report dated Aug. 14, 2014", 6 pgs.
"European Application Serial No. 12761002.0, Response filed May 6, 2014", 15 pgs.
"European Application Serial No. 12761002.0, Response filed Aug. 18, 2015", 21 pgs.
"European Application Serial No. 14811595.9, Extended European Search Report dated May 15, 2017", 9 pgs.
"European Application Serial No. 14811595.9, Response to Communication pursuant to Rules 161(2) and 162 EPC dated Aug. 17, 2016", 20 pgs.
"European Application Serial No. 14811595.9, Supplemental European Search Report dated Feb. 3, 2017", 6 pgs.
"International Application Serial No. PCT/US2011/040876, Written Opinion dated Oct. 5, 2011", 9 pgs.
"International Application Serial No. PCT/US2011/040876, International Preliminary Report on Patentability dated Jan. 3, 2013", 11 pgs.
"International Application Serial No. PCT/US2011/040876, International Search Report dated Oct. 5, 2011", 2 pgs.

(56) References Cited

OTHER PUBLICATIONS

"International Application Serial No. PCT/US2012/029430, International Preliminary Report on Patentability dated Oct. 3, 2013", 8 pgs.

"International Application Serial No. PCT/US2012/029430, International Search Report dated Jul. 11, 2012", 4 pgs.

"International Application Serial No. PCT/US2012/029430, Written Opinion dated Jul. 11, 2012", 6 pgs.

"International Application Serial No. PCT/US2014/042094, International Preliminary Report on Patentability dated Dec. 23, 2015", 7 pgs.

"International Application Serial No. PCT/US2014/042094, International Search Report dated Nov. 20, 2014", 4 pgs.

"International Application Serial No. PCT/US2014/042094, Invitation to Pay Additional Fees and Partial Search Report dated Sep. 9, 2014", 2 pgs.

"International Application Serial No. PCT/US2014/042094, Written Opinion dated Nov. 20, 2014", 5 pgs.

"Tektronix AWG710B", Anonymous, (Nov. 1, 2002).

Balle, T. J, et al., "Fabry-Perot cavity pulsed Fourier transform microwave spectrometer with a pulsed nozzle particle source", Rev. Sci. Instrum., 52, (1981), 33-45.

Brown, G. G, et al., "A broadband Fourier transform microwave spectrometer based on chirped pulse excitation", Rev Sci Instrum., 79(5), American Institute of Physics, (May 2008), 053103-1-053103-13.

Brown, Gordon, et al., "The rotational spectrum of epifluorohydrin measured by chirped-pulse Fourier transform microwave spectroscopy", Journal of Molecular Spectroscopy, 238(2), (Aug. 2006), 200-212.

Campbell, E. J, et al., "The theory of pulsed Fourier transform microwave spectroscopy carried out in a Fabry-Perot cavity: Static gas", J. Chem. Phys., 74, (1981), 813-828.

Coddington, Ian, et al., "Time-domain spectroscopy of molecular free-induction decay in the infrared", Optics Letters, vol. 35, No. 9, (2010), 1395-1397.

Crowe, T. W, et al., "Opening the terahertz window with integrated diode circuits", IEEE Journal of Solid-State Circuits, 40(10), (Oct. 2005), 2104-2110.

De Lucia, Frank C., "The submillimeter: A spectroscopist's view", Journal of Molecular Spectroscopy, 261(1), (May 2010), 1-17.

Dian, B C, et al., "Measuring Picosecond Isomerization Kinetics via Broadband Microwave Spectroscopy", Science, vol. 320, No. 5878, (May 16, 2008), 924-928.

Dian, Brian C., et al., "Seeing Is Believing: An 11 GHz molecular beam rotational spectrum (7.5-18.5 GHz) with 100 kHz resolution in 15 us measurement time", International Symposium on Molecular Spectroscopy, (Jun. 20, 2005), 29 pgs.

Douglass, K. O, et al., "Progress towards chirped-pulse Fourier transform THz spectroscopy", 64th International Symposium on Molecular Spectroscopy, Columbus, OH, [Online]. Retrieved from the Internet: <URL: http://hdl.handle.net/1811/46369>, (Jun. 21-25, 2010.), 21 pgs.

Drouin, B. J, et al., "Application of cascaded frequency multiplication to molecular spectroscopy", Rev. Sci. Instrum., 76, (2005), 093113.

Ekkers, J., et al., "Pulsed microwave Fourier transform spectrometer", Rev. Sci. Instrum., 47, (1976), 448-454.

Finneran, I. A, et al., "A direct digital synthesis chirped pulse Fourier transform microwave spectrometer", Rev Sci Instrum., 84(8), (Aug. 2013), 083104.

Gerecht, E., et al., "Chirped-pulse terahertz spectroscopy for broadband trace gas sensing", Opt Express., 19(9), (Apr. 25, 2011), 8973-84.

Gerecht, Eyal, et al., "Chirped-Pulse Terahertz Spectroscopy for Broadband Tracegas Sensing", National Institute of Standards and Technology, Optical Technology Division, (Jun. 21, 2011), 24 pgs.

Gerecht, Eyal, et al., "Recent Progress in Chirped-Pulse Fourier Transform THz Spectroscopy", NIST, (Jun. 23, 2010), 20 pgs.

Gerecht, Eyal, "Recent Progress in Chirped-Pulse Fourier Transform THz spectroscopy (with embedded notes)", NIST, (Apr. 19, 2016), 40 pgs.

Green, Sheldon, "On the amount of information in rotational relaxation experiments with application to microwave transient T1 and T2 rates", J. Chem. Phys., 69, (1978), 4076-4082.

Hahn, E. L., "Spin Echos", Physical Review, 80(1), (1950), 580-594.

Harris, Brent, et al., "Segmented Chirped Pulse Fourier Transform (CP-FT) Millimeter Spectroscopy: Identification of Volatiles by Pure Rotation", Eastern Analytical Symposium & Exposition 2012, (2012), 1 pg.

Hoke, W. E, et al., "The measurement and interpretation of T1 and T2 in the inversion doublets of 15NH3 and the rotational transitions in OCS", J. Chem. Phys., 64, (1976), 5276-5282.

Kuyanov-Prozument, K., et al., "Direct Observation of Rydberg-Rydberg Transitions in Calcium Atoms", International Symposium on Molecular Spectroscopy, (Jun. 22, 2010), 20 pgs.

Lesarri, Alberto, et al., "Interplay of Phenol and Isopropyl Isomerism in Propofol from Broadband Chirped-Pulse Microwave Spectroscopy", American Chemical Society, vol. 132, No. 38, (Sep. 7, 2010), 13417-13424.

Mata, Santiago, "A broadband Fourier-transform microwave spectrometer with laser ablation source: The rotational spectrum of nicotinic acid", Journal of Molecular Spectroscopy 280: 91-96, (2012), 91-96.

Matton, S., et al., "Terahertz spectroscopy applied to the measurement of strengths and self-broadening coefficients for high-J lines of OCS", Journal of Molecular Spectroscopy, 239(2), (Oct. 2006), 182-189.

Medvedev, I. R, et al., "Chemical analysis in the submillimetre spectral region with a compact solid state system", Analyst, 131(12), (Dec. 2006), 1299-307.

Medvedev, Ivan R, et al., "Submillimeter spectroscopy for chemical analysis with absolute specificity", Optics Letters, 35(10), (2010), 1533-1535.

Neese, C. F, et al., "Compact Submillimeter/Terahertz Gas Sensor With Efficient Gas Collection, Preconcentration, and ppt Sensitivity", IEEE Sensors Journal, 12(8), (Aug. 2012), 2565-2574.

Neill, Justin L., et al., "Next generation techniques in the high resolution spectroscopy of biologically relevant molecules", Phys. Chem. Chem. Phys., 13, (2011), 7253-7262.

Neill, Justin L., et al., "Rotational spectroscopy of iodobenzene and iodobenzene-neon with a direct digital 2-8 GHz chirped-pulse Fourier transform microwave spectrometer", Journal of Molecular Spectroscopy, (2011), 21-29.

Neill, Justin L, et al., "Segmented chirped-pulse Fourier transform submillimeter spectroscopy for broadband gas analysis", Optics Express, 21(17), (2013), 19743-19749.

Neill, Justin L., et al., "Techniques for High-Bandwidth (> 30 GHz) Chirped-Pulse Millimeter/Submillimeter Spectroscopy", (Jun. 23, 2011), 22 pgs.

Ozawa, A, et al., "High Harmonic Frequency Combs for High Resolution Spectroscopy", Physical Review Letters, vol. 100, No. 25, (Jun. 1, 2008).

Park, Barratt G, et al., "Design and evaluation of a pulsed-jet chirped-pulse milimeter-wave spectrometer for the 70-102 GHz region", AIP The Journal of Chemical Physics 135, 024202, (2011), 1-10.

Park, G. B, et al., "Design and chemical application of chirped-pulse millimeter-wave spectroscopy", 64th International Symposium on Molecular Spectroscopy, Columbus, OH,, [Online]. Retrieved from the Internet: <URL: http://hdl.handle.net/1811/38114 >, (41 pgs), Jun. 22-26, 2009.

Park, G. Barratt, et al., "Design and evaluation of a pulsed-jet chirped-pulse millimeter-wave spectrometer for the 70-102 GHz region", AIP The Journal of Chemical Physics 135, 024202, (2011), 1-10.

Pate, B. H, "Chemistry. Taking the pulse of molecular rotational spectroscopy", Science, 333(6045), (Aug. 19, 2011), 947-8.

Petkie, D. T, et al., "A fast scan submillimeter spectroscopic technique", Rev. Sci. Instrum., 68, (1997), 1675-1683.

(56) References Cited

OTHER PUBLICATIONS

Prozument, Kirill, "Chirped-Pulse Millimeter-Wave Spectroscopy of Rydberg-Rydberg Transitions", American Physical Society, (2011), 5 pgs.

Shipman, Steven T., et al., "Design and performance of a direct digital chirped-pulse Fourier transform microwave (CP-FTMW) spectrometer operating from 2-8 GHz", International Symposium on Molecular Spectroscopy, (Jun. 18, 2008), 29 pgs.

Shipman, Steven, et al., "Waveguide Chirped-Pulse FTMW Spectroscopy", (Jun. 18, 2008), 29 pgs.

Smith, Albert A, et al., "A 140 GHz pulsed EPR/212 MHz NMR spectrometer for DNP studies", Journal of Magnetic Resonance 223, [Online]. Retrieved from the Internet: <http://www.sciencedirect.com/science/article/pii/S1090780712002509>, (Jul. 20, 2012), 170-179.

Spokas, J. J, et al., "Nuclear Relaxation in Aluminum", Phys. Rev., 113,, (Mar. 15, 1959), 1462.

Steber, Amanda L, et al., "An arbitrary waveform generator based chirped pulse Fourier transform spectrometer operating from 260 to 295 GHz", Journal of Molecular Spectroscopy, 280, (3-10), Oct. 2012.

Twagirayezu, Sylvestre, "Vibrational Coupling Pathways in Methanol As Revealed by Coherence-Converted Population Transfer Fourier Transform Microwave Infrared Double-Resonance Spectroscopy", J. Phys. Chem. A, vol. 114, No. 25, (2010), 6818-6828.

Yi-Da, Hsieh, et al., "Terahertz Comb Spectroscopy Traceable to Microwave Frequency Standard", IEEE Transactions on Terahertz Science and Technology, IEEE, Piscataway, NJ, USA, XP011506303, ISSN: 2156-342X, (Apr. 19, 2013), 322-330.

Zaleski, Daniel P., et al., "A Ka-Band Chirped-Pulse Fourier Transform Microwave Spectrometer", International Symposium on Molecular Spectroscopy, (Jun. 22, 2010), 17 pgs.

Zaleski, Daniel, et al., "A Ka-band chirped-pulse Fourier transform microwave spectrometer", Article in Journal of Molecular Spectroscopy, (Oct. 2012), 10 pgs.

"Australian Application Serial No. 2014278150, First Examination Report dated Sep. 7, 2017", 4 pgs.

\* cited by examiner

CHIRPED PULSE FREQUENCY-DOMAIN COMB FOR SPECTROSCOPY

CLAIM OF PRIORITY

This application is a continuation of U.S. patent application Ser. No. 14/718,624, titled "CHIRPED PULSE FREQUENCY-DOMAIN COMB FOR SPECTROSCOPY," filed on May 21, 2015, which is a continuation of U.S. patent application Ser. No. 13/704,483, titled "CHIRPED PULSE FREQUENCY-DOMAIN COMB FOR SPECTROSCOPY," filed on Feb. 27, 2013, which was a U.S. National Stage Filing under 35 U.S.C. § 371 from International Patent Application Serial No. PCT/US2011/040876, titled "CHIRPED PULSE FREQUENCY-DOMAIN COMB FOR SPECTROSCOPY," filed on Jun. 17, 2011, and published on Dec. 22, 2011 as WO 2011/160013 A1, which claims the benefit of priority of U.S. Provisional Patent Application Ser. No. 61/355,862, titled "Chirped Pulse Frequency-domain combs (CPFC) for Spectroscopy from Microwave to Infrared," filed on Jun. 17, 2010, the benefit of priority of each of which is presently claimed hereby, and each of which is hereby incorporated by reference herein in its entirety.

STATEMENT REGARDING FEDERALLY SPONSORED RESEARCH OR DEVELOPMENT

This invention was made with government support under Grant No. CHE-0215957 (MRI Program), CHE-0618755 (CRIF:ID Program), and CHE-0847919 (CCI Program), awarded by the Chemistry Division (CHE) of the National Science Foundation (NSF). The government has certain rights in the invention.

BACKGROUND

Spectroscopy, such as rotational spectroscopy, is a powerful structural tool in physical chemistry. For example, the relationship between the molecular structure and the rotational transition frequencies can be used for structure determination of gas phase samples. Other effects in the rotational motion of molecules, such as centrifugal distortion, hyperfine spectral structure from quadrupolar nuclei, or frequency shifts caused by tunneling motion, can be used to provide further characterization of the molecular structure and low frequency vibrational motions. Microwave spectrometers, such as using a waveguide, generally limit the size range of molecules that can be interrogated by pure rotational spectroscopy, such as because of the need for sufficient vapor pressure in the waveguide cell.

A molecular beam, Fabry-Pérot, Fourier transform microwave (FTMW) spectrometer can be used to perform time-domain microwave spectroscopy to provide sensitive detection of the rotational free induction decay (FID), such as following polarization by a microwave pulse. Such time-domain spectroscopy can achieve high frequency resolution without power broadening or the line shape distortion associated with the waveguide-based approach discussed above. Pulsed molecular beam sources have expanded the range of molecular systems amenable to analysis by rotational spectroscopy. Generally, the Fabry-Pérot FTMW spectrometer is a narrowband spectrometer. For example, the use of a cavity with high quality factor generally limits the measurable frequency bandwidth to less than 1 megahertz (MHz) in generally-available spectrometer designs. The microwave cavity serves two functions: it decreases the power requirements for the microwave polarizing pulse and it enhances the amplitude of the FID emission signal. Often these spectrometers are called "broadband" to indicate that they operate over a wide frequency range, typically about 10 gigahertz (GHz). However, the process of acquiring a spectrum over the full operating range of the spectrometer is laborious. The spectrum scanning process generally involves a series of steps where the cavity is precisely tuned to resonance, a narrow frequency range is measured (e.g., 500 kilohertz (kHz)), and the cavity is moved to its next position in the frequency tuning series.

A spectrum spanning a frequency range of several GHz can be obtained, but the Fabry-Pérot spectrometer design leads to long spectrum acquisition times (e.g., many hours). A major contributor to the overall measurement time comes from the positioning of the cavity mirrors at each frequency step. The time-consuming spectral acquisition process poses difficulties for using FTMW spectroscopy in analytical chemistry applications, for optimizing source conditions for previously unknown species, or for performing rotational spectroscopy of excited vibrational or electronic states prepared by laser.

OVERVIEW

In one approach, frequency-domain combs can be established by laser pulse trains, such as provided by mode-locked lasers. Such frequency-domain combs have a wide range of applications in spectroscopy and metrology, such as for observation of the rotational spectrum of gas phase molecules. The main difficulties with the mode-locked laser approach include the low pulse energies associated with individual frequency-domain combs and the non-robust nature of the basic laser light sources. Such laser-based approaches face challenges in extending operation into desired ranges of frequencies, such as into the chemically important frequency range of between about 3-30 terahertz (THz).

Advances in high-speed digital electronics and in other solid-state devices (e.g., amplifiers, mixers, frequency multipliers, or other devices) have increased the bandwidth capabilities of a solid-state device approach. Such an approach can be used for spectroscopy. In this approach, the light source for spectroscopy can include an arbitrary waveform generator (AWG) circuit. In an example, energy for sample excitation can be provided by frequency upconversion of an output of an AWG using a broadband mixer, such as coupled to a frequency multiplier. The AWG circuit, broadband mixer, or frequency multiplier can include solid state devices, without requiring the use of mode-locked lasers, unlike other approaches.

The present inventors have developed, among other things, apparatus and techniques to generate phase-controlled time-domain signals, such as using a solid-state electronic apparatus. Such time-domain signals can be used to establish frequency-domain combs including electromagnetic energy for excitation of samples for analysis or spectroscopy, such as at frequencies of less than 1 GHz to more than 1 THz (e.g., to provide a frequency-domain comb "light source.").

One approach for performing microwave spectroscopy includes chirped-pulse Fourier transform microwave spectroscopy (CP-FTMW). In cases where the peak power is limited by a system component (e.g., the amplifier), the chirped pulse provides a way to deliver enhanced pulse energy for a broadband pulse while still providing a fixed time duration, in contrast to other approaches. In an example, a "macropulse" train of chirped pulses can be used to establish a frequency-domain comb. The pulse train waveform can use a 100% duty cycle and therefore, delivers maximum pulse energy to the macropulse (and, therefore, to each frequency-domain comb peak). The individual pulses ("micropulses") can include chirped pulses having linear frequency sweep (or a quadratic phase sweep).

In an example, AWG-generated chirped pulses can allow separate control of a frequency-domain comb bandwidth, a frequency-domain comb separation, or a frequency-domain comb resolution, among other parameters. For example, a time duration of the time-domain pulse can be specified in relation to one or more physical properties of a system or sample being characterized by the spectroscopy, such as the dephasing (or "$T_2$") time). A chirped pulse (e.g., a "micropulse") can be multiplied by a frequency multiplier without changing the basic pulse time structure, such as for allowing upconversion of a frequency-domain comb established by a train of such chirped pulses while still preserving a desired frequency-domain comb peak separation. In an example, the bandwidth of the comb structure can be expanded using a frequency multiplier.

In an example, one or more of a chirped pulse (micropulse) or a pulse train (macropulse) can be shaped, such as using a specified window profile (e.g., a specified window function or envelope shape). For example, a tapered cosine window function can be applied to one or more of the micropulses, such as to prevent the established comb peaks from having a long "tail" leaking into adjacent comb peaks.

In an example, an overall pulse shape envelope can be applied to the macropulse such as to adjust or reduce the line width at baseline for individual comb peaks. Such pulse shaping (e.g., a Kaiser-Bessel window, or other shape) can be applied to the macropulse when generated or to the detected pulse train after signal digitization following either direct or down converted detection, such as using a mixer. Such macropulse shaping can reduce the signal leakage into adjacent frequency channels, such as facilitating compression of the measurement bandwidth through offset comb mixing. Such offset comb-mixing can be used to provide a broadband microwave-to-THz (or beyond) detection system using multiplexing of signal detection. For example, a downconverted frequency-domain comb signal can include interleaved comb peak frequencies for detection, such as to compress the bandwidth of a response signal for digitization or detection while still preserving the ability to measure a unique response corresponding to each stimulus comb peak.

The present inventors have recognized, among other things, that the use of solid-state devices can provide compact and field-portable spectroscopic apparatus or light sources. Such techniques can provide a light source for spectroscopy that can enable a new generation of broadband spectrometers, such as can include multiplexed detection at each comb frequency. For example, without being bound by theory, solid-state frequency multiplication techniques can be used with a portion of the apparatus or techniques described herein, such as to support spectroscopy in the "fingerprint" region of the infrared spectrum (from about 100 to about 1000 $cm^{-1}$ or from about 3 to about 30 THz), such as using a time-domain pulse train provided by an AWG.

Chirped-pulse spectrometers, establishing frequency-domain combs, can be used to measure the pure rotational spectrum, the vibrational spectrum (vibration-rotation in gas phase), or the electron spin resonance spectrum (often useful in biophysical chemistry applications) of complex mixtures of molecules, affording both high sensitivity and high selectivity for molecular detection for quantitative chemical analysis of samples.

This overview is intended to provide an overview of subject matter of the present patent application. It is not intended to provide an exclusive or exhaustive explanation of the invention. The detailed description is included to provide further information about the present patent application.

Figure 1:
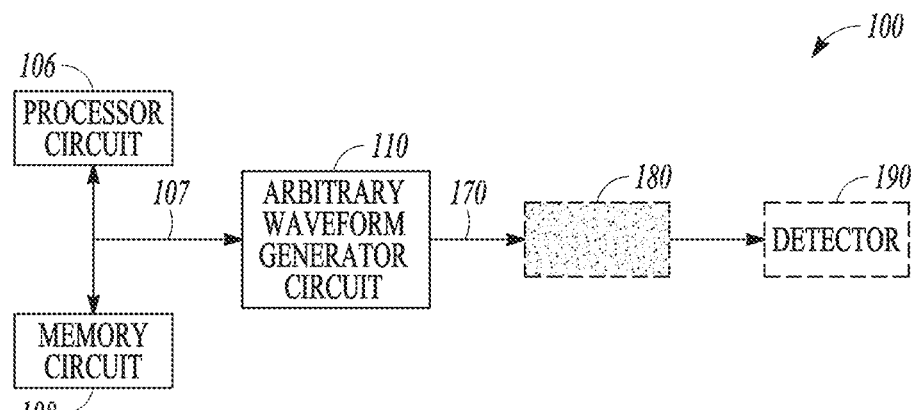
FIG. 1 illustrates generally an example of at least a portion of a system that can include an arbitrary waveform generator (AWG), such as coupled to a processor circuit and a memory circuit.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have developed apparatus and techniques such as for providing a source of electromagnetic energy (e.g., a "light source") using a chirped pulse frequency-domain comb (CPFC) technique, such as for spectroscopy, and apparatus and techniques for detection of a response, such as using a multiplexed detection scheme (e.g., interleaved mixing). Generally, an absorption spectrometer includes a sample interaction region where absorption of light from the light source takes place. A response spectrum can be obtained from the absorption by the sample at frequencies corresponding to one or more peaks included in a frequency-domain comb established by a pulse train of chirped pulses. The amplitude and the phase of information corresponding to detected comb peaks can include information relevant to spectroscopy.

For example, at microwave frequencies, the absorption region (e.g., a sample region) can be enclosed in a waveguide system to help propagate the light from the light source. However, a free space arrangement, such as using broadcast and receive antennas, can also be used. As the frequency increases toward the infrared, quasi-optical arrangements of the spectrometer interaction region can be used. Such systems can include using optical techniques or apparatus to increase an effective absorption path length through the sample, such as including multipass optics (e.g., a White or Heriott cell) or mirror cavities (e.g., cavity-enhanced absorption or ring-down techniques).

In an example, the frequency-domain comb structure established by an AWG can be coupled to an external cavity to perform cavity-enhanced spectroscopy such as to increase detection sensitivity. At a fixed condition, such a cavity generally transmits radiation in a frequency-domain comb; the cavity-generated comb can be matched to the frequency-domain comb established by the AWG. These two combs can then more efficiently use the energy generated by an amplifier. In an example, the AWG-generated comb can be modified to create frequency-domain components that need not be exactly evenly spaced, allowing for compensation in response to a frequency dependence of the free spectral range of the cavity. It is believed to not presently be possible to do this with optically generated combs.

In an example, spectrum detection can be multiplexed, such as for offering significantly reduced measurement times to acquire a broadband spectrum as compared to purely cavity-based approaches. Such capability opens new possibilities for time-resolving changes in a sample environment, such as for monitoring applications or for following the time course of reactions in application related to analytical chemistry.

For example, spectrometers using an AWG-established frequency-domain comb can be configured for operation in acquiring spectra in the mm-wave or sub-mm wave frequency ranges where signals can be strongest for room-temperature gas samples. Spectrometers in this frequency range can be used to observe the rotational spectrum of gas phase molecules. The high specificity of the rotational spectrum makes this approach a candidate for high-throughput chemical screening of complex mixtures. One example of such an application is breath analysis as a medical diagnostic. Spectrometers operable in such ranges of frequencies can also be used for work related to radio astronomy.

The wavelength or frequency range (e.g., sub-mm-to-THz) can also be useful in biological analysis. The ability to acquire a broadband spectrum "instantaneously" can have a significant impact on this field. For example, such spectroscopy can be used to simultaneously and quantitatively monitor complex chemical mixtures, such as for chemical process control. This can allow a manufacturer to increase yield or, often more importantly, to maintain purity by minimizing production of unwanted or even toxic side products.

FIG. 1 illustrates generally an example of at least a portion of a system 100 that can include an arbitrary waveform generator (AWG) 110, such as can be coupled to a processor circuit 106 and a memory circuit 108. The memory circuit 108 can include instructions, such as can be performed by the processor 106 to control one or more aspects of the operation of the AWG 110, or to perform one or more other techniques to control or configure a spectrometer apparatus to generate a stimulus or acquire a response, such as including analog or digital processing to determine a resulting absorption or emission spectrum of a sample in response to stimulus provided at least in part using the AWG 110.

In an example, a bus 107 can couple the processor 106 to the memory circuit 108, or to the AWG 110. For example, the AWG 110 can generate a specified or desired time-domain waveform, such as by using a pattern stored in the memory circuit 108. The AWG 110 can include, or can be coupled to, a high-accuracy frequency standard such as can be derived from a precision oscillator. The AWG 110 can be solid-state, such as using high-speed digital and analog semiconductor technology to provide a specified output waveform in a reproducible and phase-controlled manner (e.g., a phase error between successive pulses or pulse trains provided by the AWG 110 can be controlled or specified). In this manner, chirped pulses, or pulse trains, can be provided having precisely controlled timing within the pulse or within the pulse train, or between pulses or between pulse trains (e.g., the AWG 110 can provide waveforms having controlled phase or a desired phase coherence). Unlike other approaches including using frequency-domain combs generated using laser systems, the AWG 110 output can be triggered on demand. Such triggering capability can make it easy to synchronize broadband spectral monitoring using the AWG 110 as a source triggered by other events (such as to sample a reaction, the reaction initiated via a pulsed laser source, or other events).

In an example, the AWG 110 can be used to provide a time-domain train of chirped pulses that establish a corresponding frequency-domain comb at an output 170 of the AWG 110, such as discussed below in the examples of FIG. 3A-C, 4A-C, 5A-C, 6A-C, 7A-C, 8A-B, or 9, such as to irradiate a sample included in a sample region 180. A resulting emission or absorption spectrum (e.g., a time-domain response) can then be acquired such as using a detector 190 (e.g., a digitizer, or one or more other detection circuits). An amplifier, such as a traveling wave tube amplifier (or other broadband high-frequency amplifier) can be included in or coupled to the AWG 110, such as to increase an intensity of radiation provided to the sample included in the sample region 180. In an example, the detector 190 can include a low-noise amplifier (LNA) or other circuitry, such as to receive or amplify a time-domain response from the sample region 180 after stimulation by a frequency-domain comb established at least in part using the AWG 110.

Examples of AWGs can provide output samples comprising an output waveform at a maximum rate of about 1 to 30 gigasamples (Gs) per second, such as depending on a desired amplitude resolution, such as to provide a "baseband" output. If the baseband output frequency range of the AWG 110 is outside a desired range for spectroscopy, one or more of a mixer or a frequency multiplier can be used, such as to adjust the bandwidth or frequency range of a frequency-domain comb established by the AWG 110. One or more filters or amplifiers can then be used, such as to reject unwanted sidebands, and to amplify the frequency-domain comb established by the AWG 110.

Figure 2:
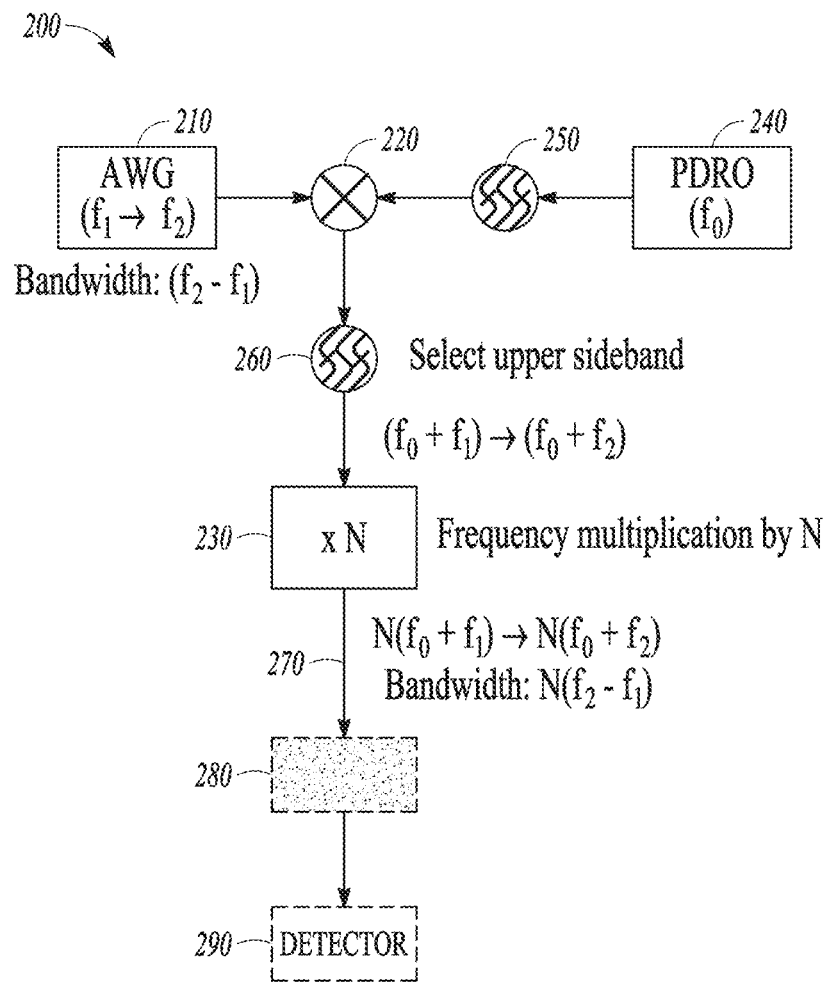
FIG. 2 illustrates generally an example of at least a portion of a system that can include an AWG, such as coupled to a mixer and a frequency multiplier.

FIG. 2 illustrates generally an example of at least a portion of a system 200 that can include an AWG 210, such as coupled to a first mixer 220 and a frequency multiplier 230. In the example of FIG. 2, a waveform generated by the AWG 210 can include a chirped pulse (e.g., micropulse), sweeping from a first frequency, "$f_1$," to second frequency, "$f_2$," (e.g., a first range of frequencies between $f_1$ and $f_2$) to provide a corresponding first specified bandwidth. The output of the AWG 210 can be upconverted, such as to a higher second range of frequencies (e.g., a microwave frequency range), such as by using a broadband mixer (e.g., the first mixer 220) and a phase-locked dielectric resonator oscillator (PDRO) 240 or other suitable single-frequency source (e.g., a microwave synthesizer, or other source), the oscillator providing an LO frequency, "$f_0$."

The AWG 210 can provide an output signal to the first mixer 220 at an intermediate frequency (IF) port and the PDRO 240 can be coupled to a local oscillator (LO) port of the first mixer 220, such as via a first filter 250 (e.g., a band-pass filter or other filter configuration). In an example, at the output of the first mixer 220, a single sideband from the mixer output can be selected, such as by using a second filter 260 (e.g., a band-pass filter or other filter configuration). The time-domain signal at the output of the second filter 260 can include an upper sideband from ($f_0+f_1$) to ($f_0+f_2$).

The selected single sideband output (e.g., the upper sideband) can be provided to the frequency multiplier 230 (e.g., with factor of "N" multiplication). The frequency multiplier 230 can increase the bandwidth of each chirped pulse (e.g., micropulse), such as by a multiplication factor (N), such as without altering the time structure of the pulse train (e.g., a duration of a chirped pulse can remain the same before and after the multiplication), such as to provide a wider second specified bandwidth of the frequency-domain comb, $N(f_2-f_1)$.

Because the "light source" uses the AWG 210 and PDRO 240 (or other oscillator), and both can be locked to a high stability and high accuracy clock, the frequency accuracy of stimulus waveform or detected response can both be high, and acquisition of the spectrum does not require special calibration (using etalons, for example). This can be contrasted to optical frequency-domain combs generated by a laser, where a complex system is generally required to stabilize the frequency of the individual combs.

Figure 3A:
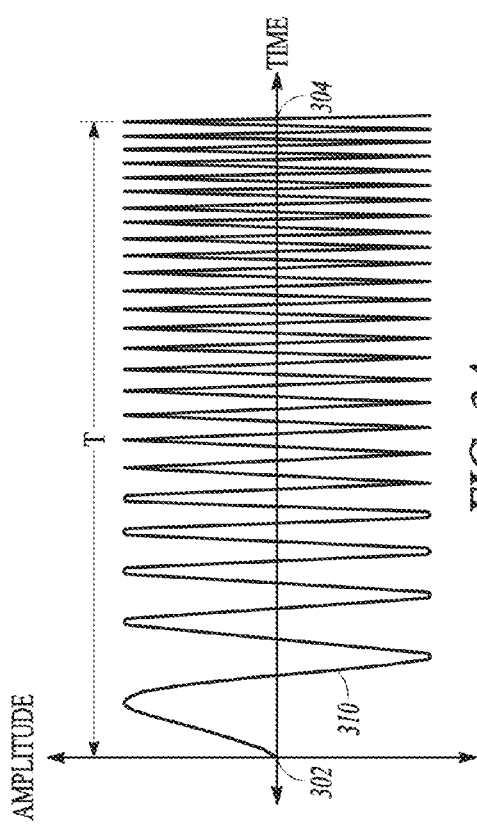
FIGS. 3A-C illustrate generally conceptual examples of a chirped pulse, a train of chirped pulses, and a corresponding frequency-domain comb that can be established by the train of chirped pulses.
Figure 3B:
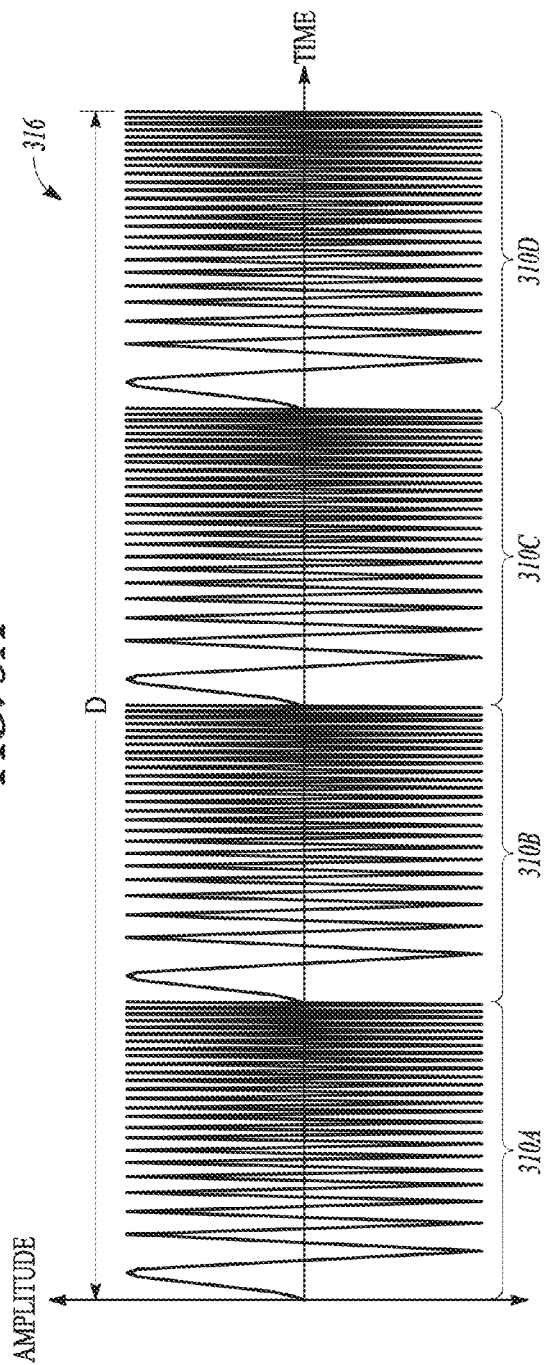
Figure 3C:
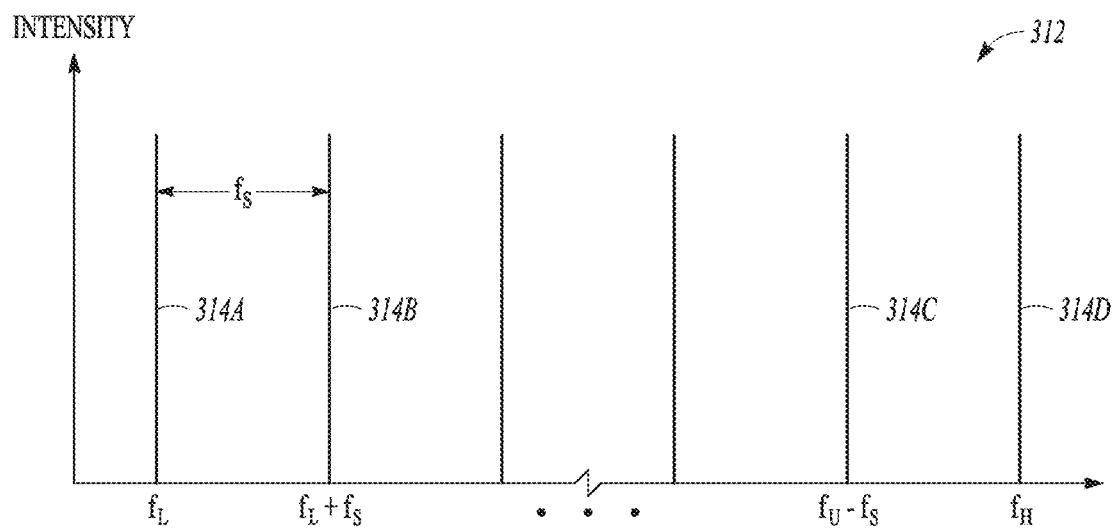

FIGS. 3A-B illustrate generally illustrative examples of a chirped pulse 310, a train of chirped pulses 316 including chirped pulses 310A-D, and a corresponding frequency-domain comb 312 that can be established by the train of chirped pulses 316. The chirped pulse frequency-domain comb 312 (CPFC) can be established using a high-speed AWG configured to provide the pulse train 316, such as discussed in the examples of FIGS. 1-2.

The individual chirped pulses 310A-D (e.g., micropulses) in the pulse train 316 can be used to independently control a frequency-domain comb bandwidth and frequency-domain comb peak separation (e.g., a frequency comb "spacing"). For example, the chirped pulse 310 can include a frequency sweep across a first specified bandwidth including a start frequency (e.g., at 302) and stop frequency (e.g., at 304) included in the chirp's linear (in this example) frequency sweep.

The frequency-domain comb 312 established using the pulse train 316 can include frequency-domain comb peaks 314A-D. The frequency-domain comb peak spacing, "$f_s$," can be established by the reciprocal of the micropulse (e.g., chirped pulse 310) duration, "T." In an illustrative example, a 100 nanosecond micropulse duration will establish a frequency-domain comb spacing of 10 MHz. The chirped pulse 310 can be repeated to generate the pulse train 316. A total duration of the pulse train 316 (e.g., the macropulse duration, "D") can establish a line width of a frequency-domain comb peak (e.g., a frequency resolution of the comb). In an example, a bandwidth of the frequency-domain comb 312 can include a range from a first frequency, "$f_l$," corresponding to the start frequency of the chirped pulses, to a second frequency, "$f_h$," corresponding to the stop frequency of the chirped pulses.

Figure 4A:
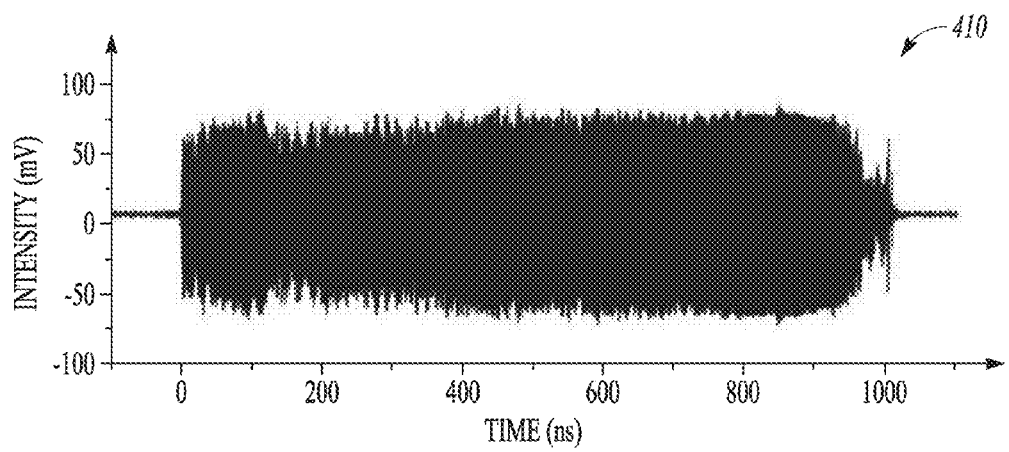
FIGS. 4A-C illustrate generally illustrative examples of a chirp pulse, a corresponding experimentally-obtained frequency-domain spectrum, and a spectrogram including a time-frequency diagram corresponding to the chirp pulse.

FIG. 4A illustrate generally illustrative example of an amplified chirped pulse 410, such as generated by an AWG, upconverted by a mixer, frequency multiplied, filtered, and amplified such as by using a TWT amplifier. In an example, one or more other amplifier configurations can be used, such as a solid-state amplifier. Such a solid-state amplifier can include one or more semiconductor materials, such as a compound semiconductor material (e.g., Gallium Nitride (GaN) or one or more other materials).

Figure 4B:
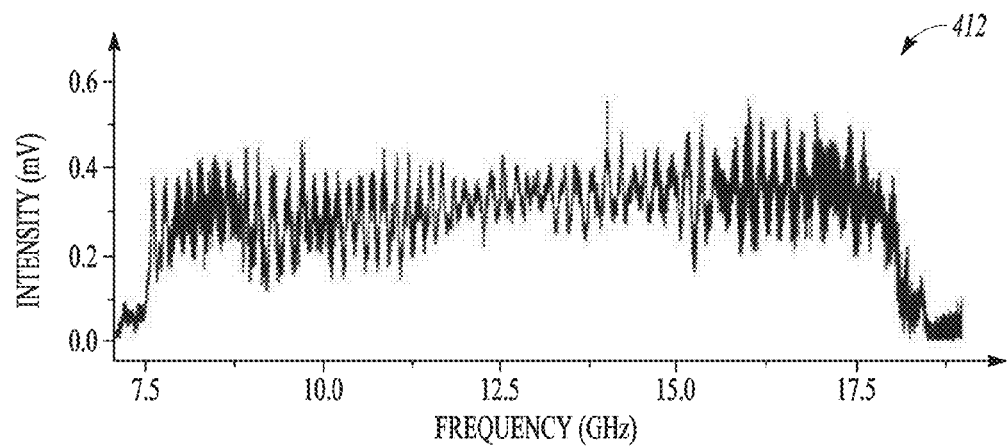
Figure 4C:
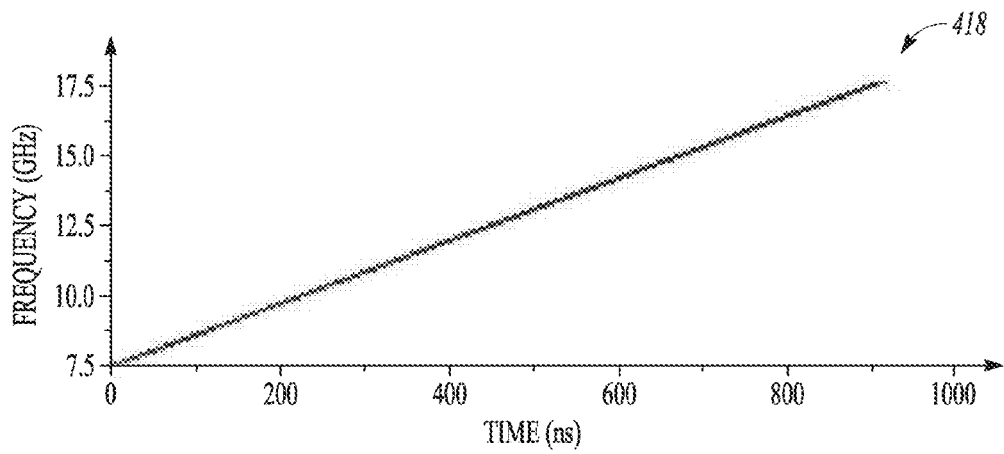

FIG. 4B illustrates generally an illustrative example of a corresponding frequency-domain spectrum 412, and a spectrogram 418. The chirped pulse 410 can include a sweep from a first frequency (e.g., 7.5 GHz) to a second frequency (e.g., 17.5 GHz), such as over a chirped pulse duration of about 1 microsecond (e.g., shorter than a free-induction decay (FID) or other duration of interest in relation to the sample characteristic being analyzed). The corresponding frequency-domain spectrum 412 includes a range from 7.5 GHz to 17.5 GHz, corresponding to the range of frequencies included in the linear sweep of the chirped pulse 410. FIG. 4C illustrates generally an illustrative example of a spectrogram 418 including the time-frequency relationship of the energy included in the time-domain chirped pulse 410, such as including a linear sweep over time. The chirped pulse 410 can be included in a sequence of successive pulses comprising a pulse train, such as to establish a frequency-domain comb such as discussed in the examples above and below.

Figure 5A:
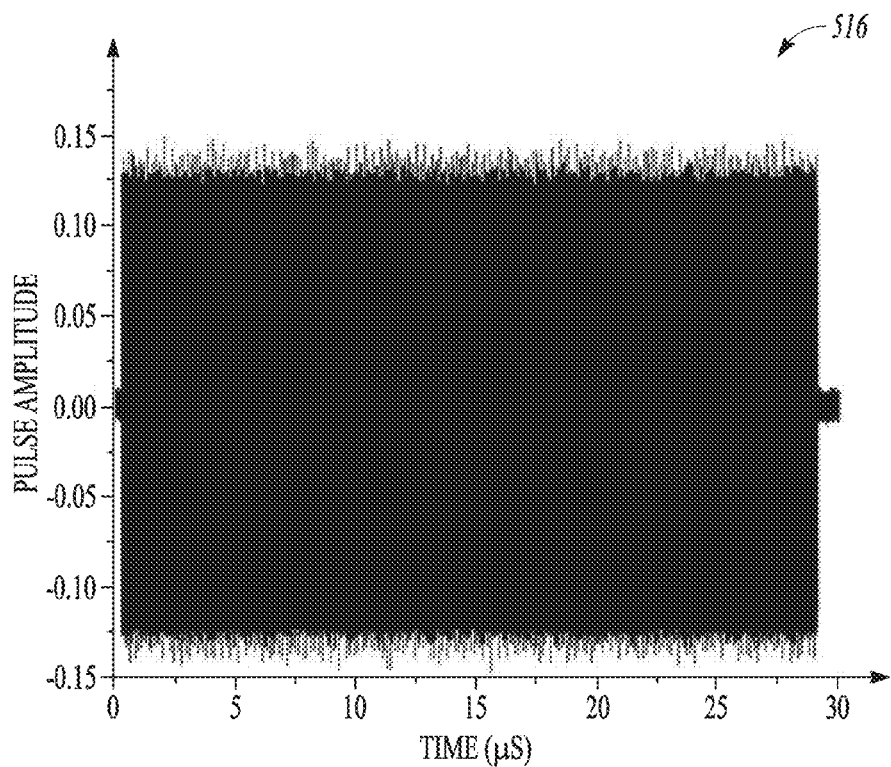
FIGS. 5A-C illustrate generally illustrative examples of a train of chirped pulses, a corresponding experimentally-obtained frequency-domain comb established by the train of chirped pulses, and a more detailed view of a portion of the frequency-domain comb illustrating generally a separation between frequency-domain comb peaks.
Figure 5B:
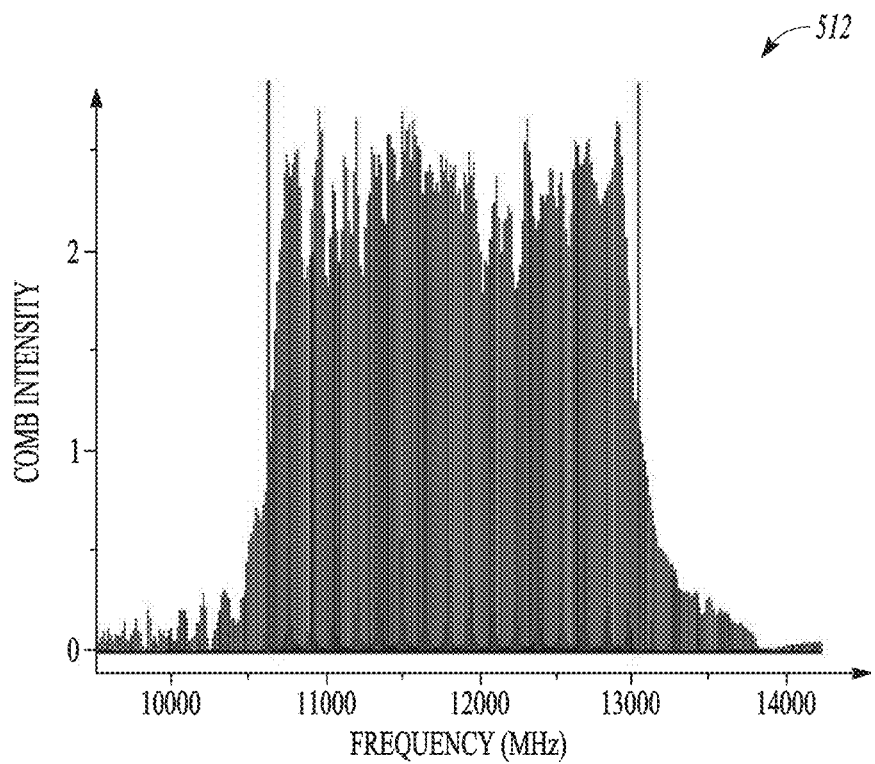
Figure 5C:
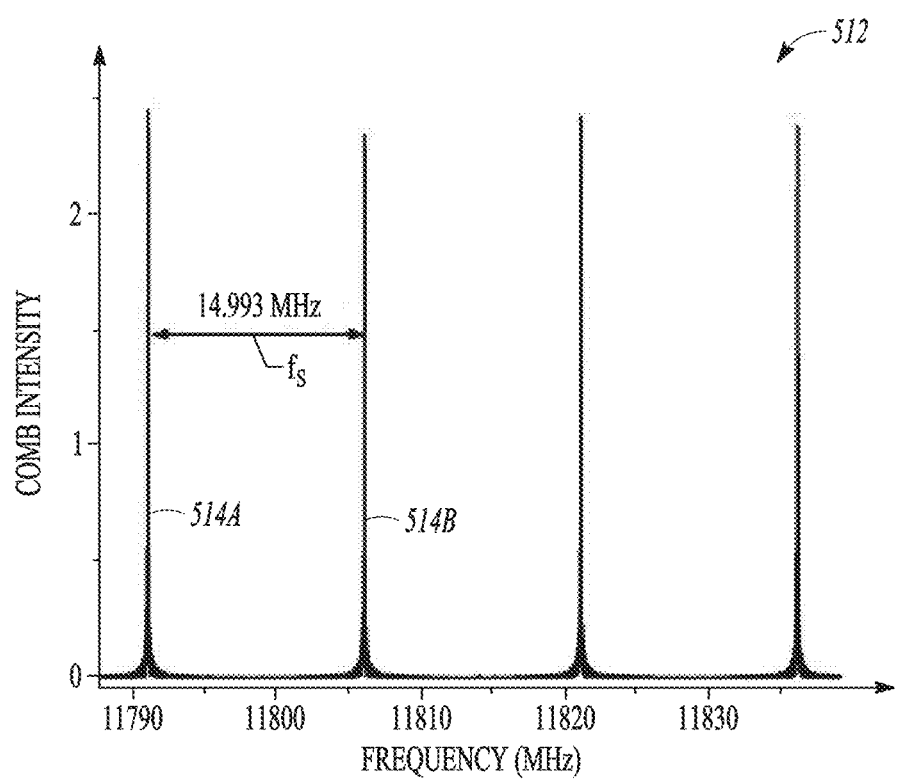

FIGS. 5A-C illustrate generally yet more illustrative examples of a train of chirped pulses 516, a corresponding frequency-domain comb 512 that can be established by the train of chirped pulses 516, including a more detailed view of a portion of the frequency-domain comb 512 in FIG. 5C illustrating generally a separation between frequency-domain comb peaks, "$f_s$."

In the illustrative example of FIGS. 5A-C, the pulse train 516 can include a sweep across a first specified bandwidth of about 2.4 GHz (e.g., a sweep from about 1.0 GHz to about 3.4 GHz), such as including a chirped pulse duration of about 66.7 nanoseconds (ns), including 430 pulse repetitions for a total pulse train 516 duration of about 28.7 microseconds. In the example of FIGS. 5B-C, the frequency-domain comb 512 is established via upconversion of the time-domain chirped pulses from a baseband frequency range of about 1 GHz, to a range from about 10.64 GHz to about 13.04 GHz, such as using a 14.04 GHz phase-locked dielectric resonator oscillator (PDRO). In this example, the separation between frequency-domain comb peaks, such as between a first comb peak 514A and a second comb peak 514B is about 14.993 MHz, corresponding to the reciprocal of the chirped pulse duration of about 66.7 ns.

Figure 6A:
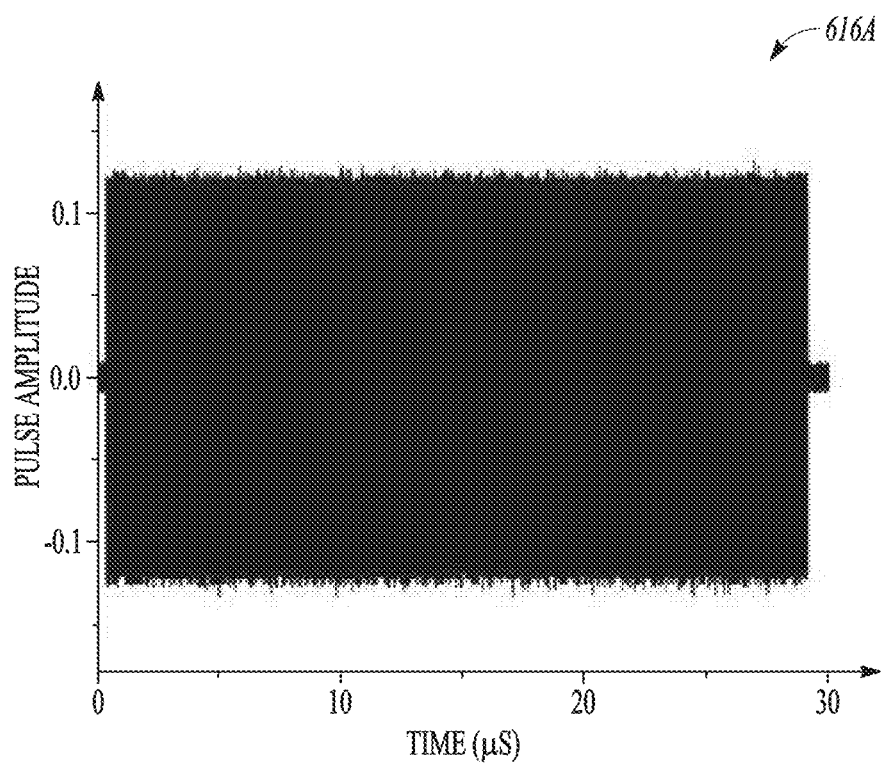
FIGS. 6A-C illustrate generally illustrative examples of a train of chirped pulses simulated with and without time-domain pulse shaping, and a corresponding comparison between simulated frequency-domain combs that can be established by the respective trains of chirped pulses.
Figure 6B:
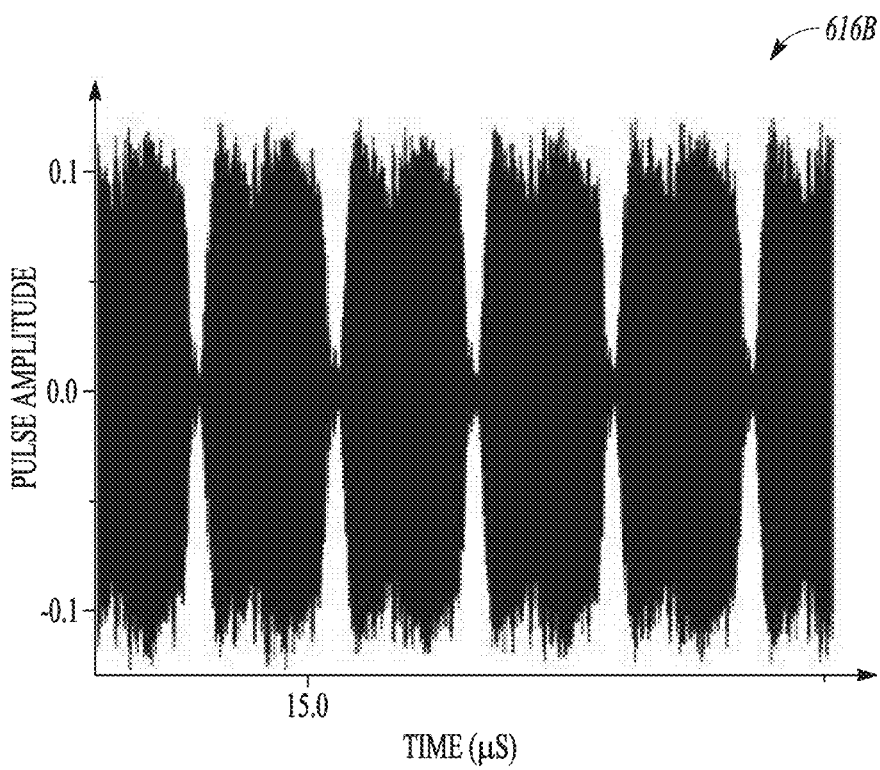
Figure 6C:
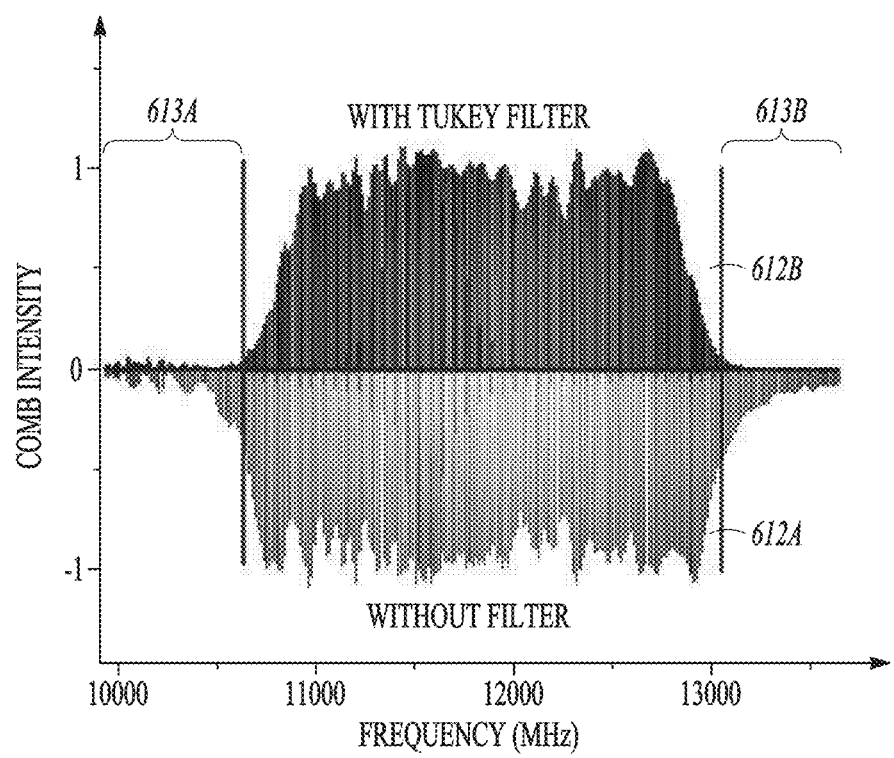

FIGS. 6A-C illustrate generally illustrative examples of a first train of chirped pulses 616A without time-domain chirped-pulse envelope shaping, and a second train 616B including time-domain chirped-pulse envelope shaping, and a corresponding comparison between the frequency-domain combs established by the respective trains of chirped pulses. The frequency range over which combs with significant power are established depends on the overall shape of the chirped pulse (e.g., micropulse). The frequency-domain comb bandwidth localization can be modified or improved, such as by applying a tapered cosine window function (e.g., including a parameter, α=0.25) to each micropulse in the pulse train. Other signal windows can be used to shape the comb envelope as desired.

The shaped pulses included in the second pulse train 616B include shaping (e.g., time-domain multiplication) of the chirped pulses with a windowing function (e.g., a Tukey or tapered cosine window in this illustrative example). Other window shapes can be used. In the illustrative example of FIG. 6C, the first pulse train 616A establishes a frequency-domain comb 612A, such as including wings 613A-B leaking into the adjacent spectrum, which can be undesirable. In comparison, the second frequency-domain comb 612B includes greatly suppressed sideband energy in the region of the wings 613A-B, such as provided at least in part by the time-domain pulse shaping of the second pulse train 616B of FIG. 6B.

Figure 7A:
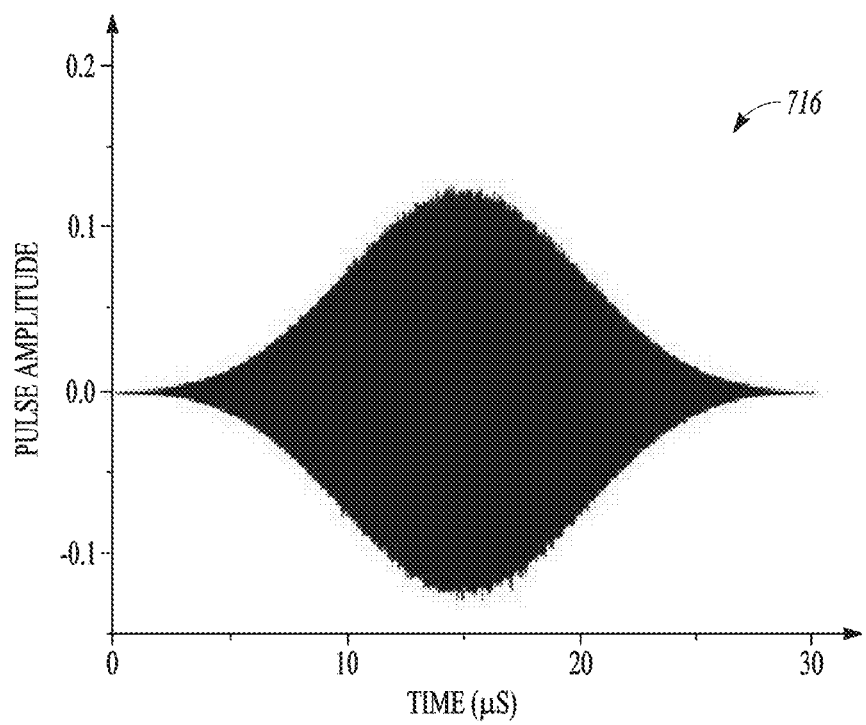
FIGS. 7A-C illustrate generally illustrative examples of simulated time-domain pulse shaping of a chirped pulse, and a corresponding comparison between simulated frequency-domain combs and comb peaks that can be established by a pulse train of shaped chirped pulses as compared to a pulse without such pulse shaping.
Figure 7B:
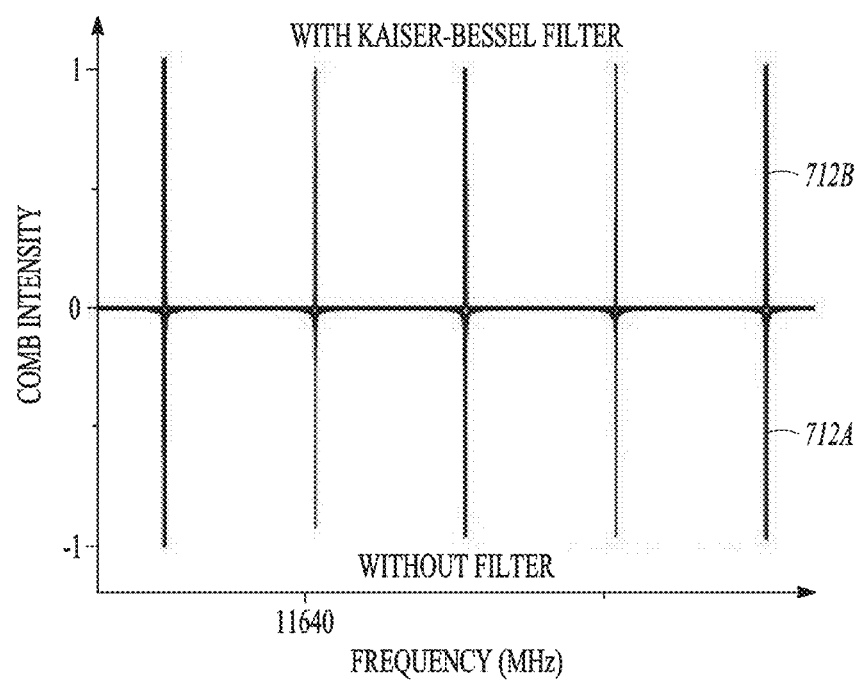
Figure 7C:
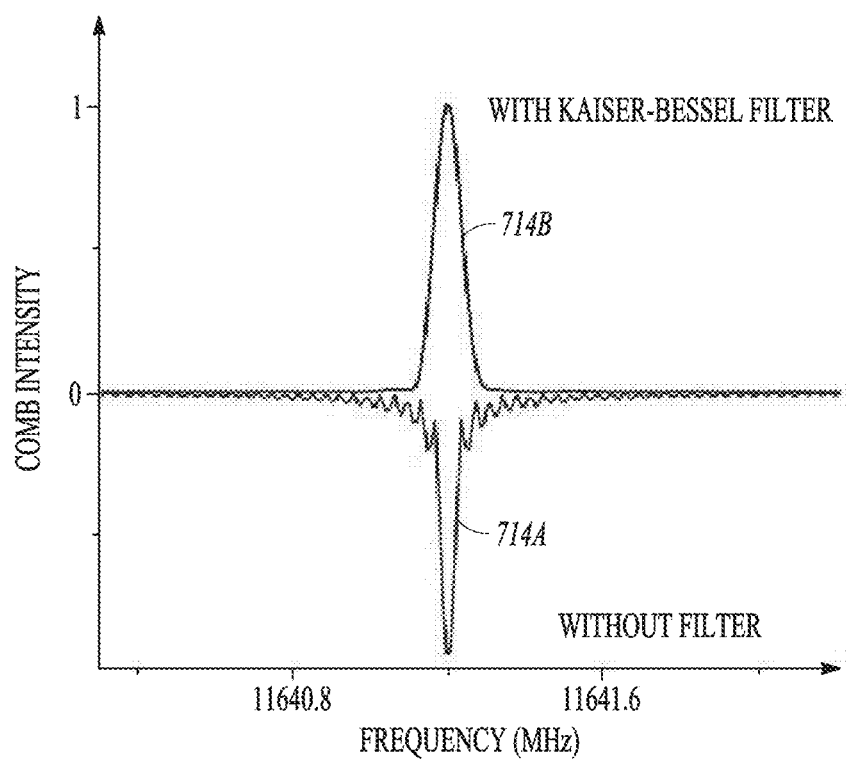
Figure 8A:
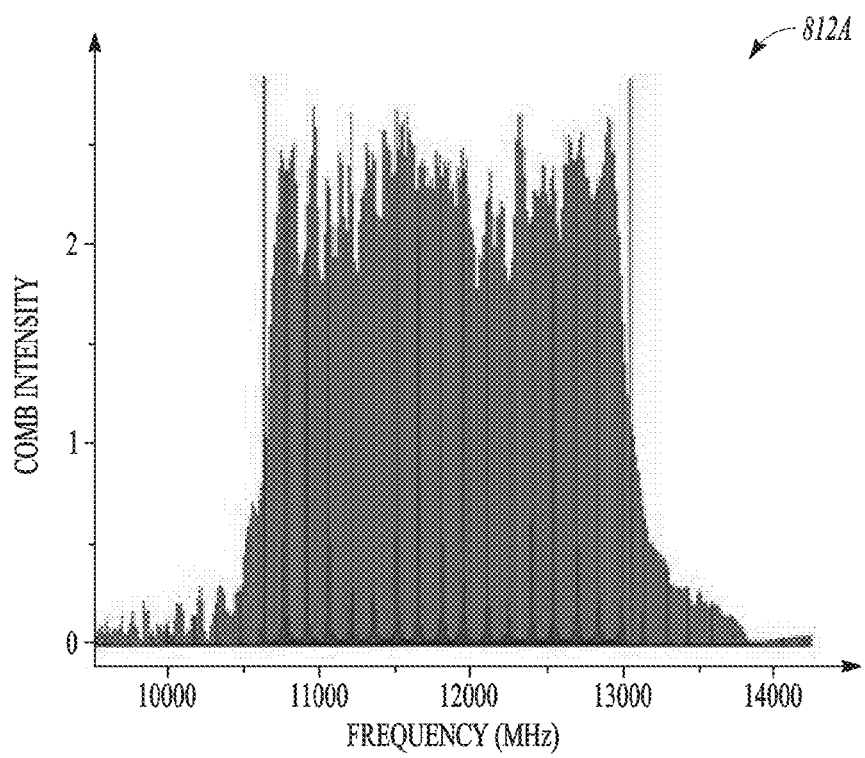
FIGS. 8A-D illustrate generally illustrative examples of experimentally-obtained frequency-domain combs before and after frequency multiplication of the corresponding time-domain chirped pulse train.
Figure 8B:
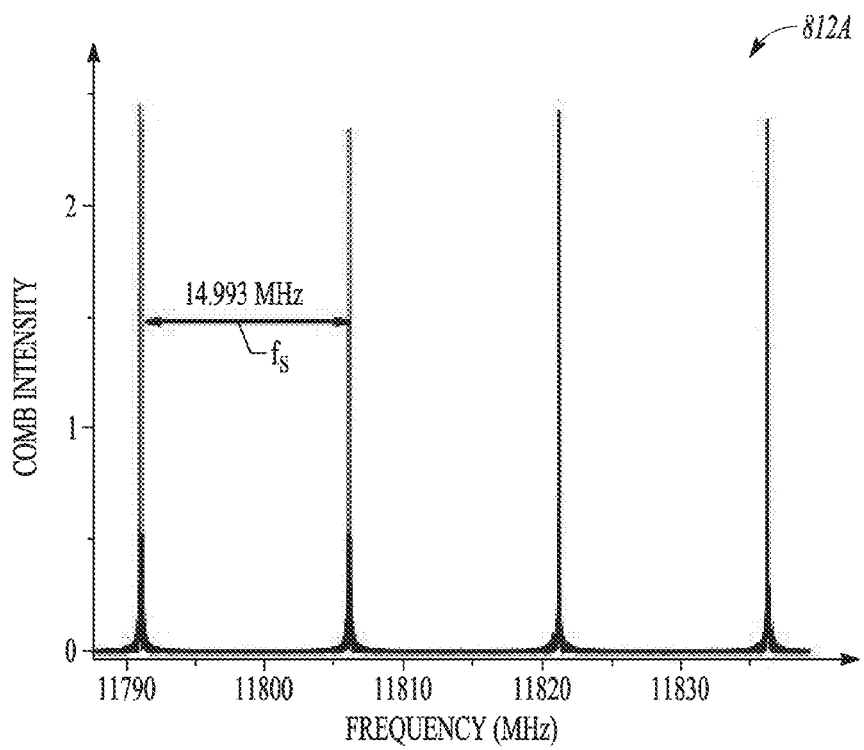
Figure 8C:
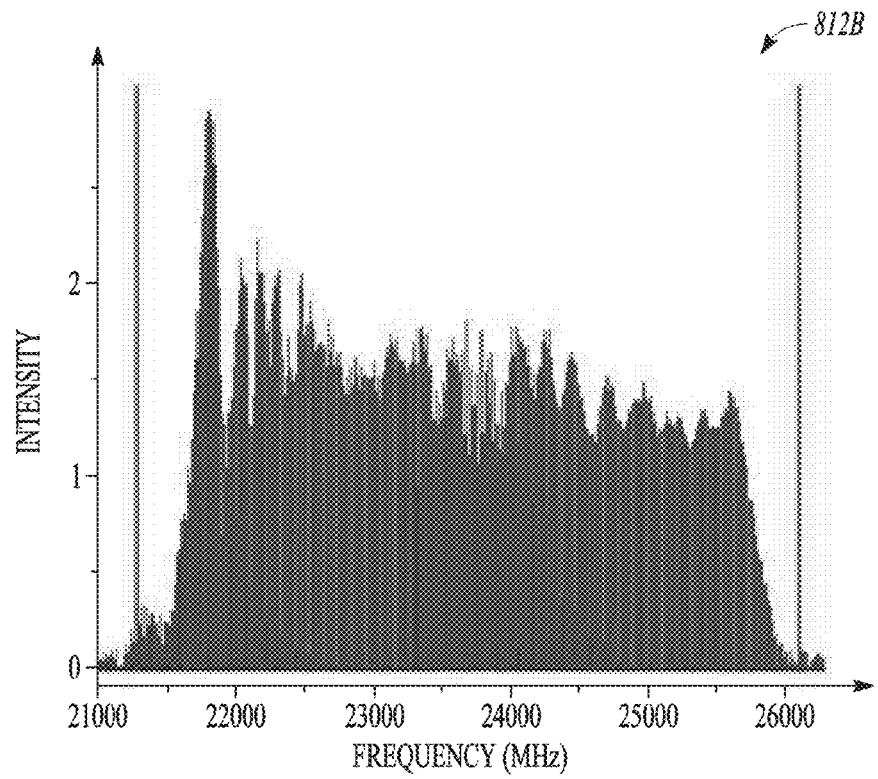
Figure 8D:
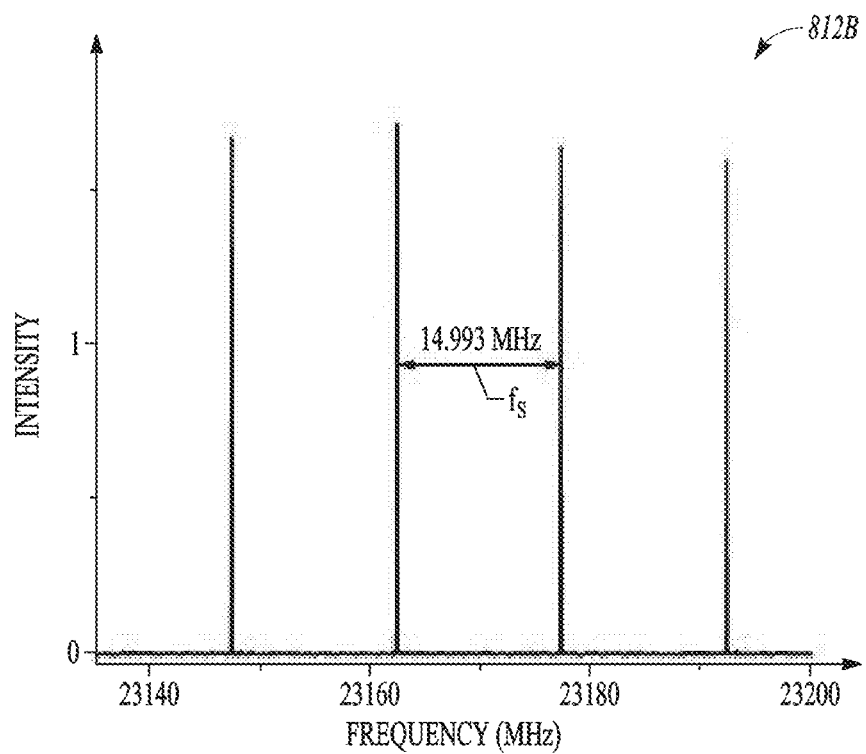

FIGS. 7A-C illustrate generally illustrative examples of time-domain pulse shaping of a chirped pulse, and a corresponding comparison between the frequency-domain combs and comb peaks established by a pulse train of shaped chirped pulses as compared to a frequency-domain comb generated without such pulse shaping.

A frequency-domain line shape of the individual frequency-domain comb peaks (e.g., the "teeth" of the frequency-domain comb) can be controlled by adjusting an overall pulse shape of the pulse train (e.g., by shaping the macropulse envelope rather than or in addition to shaping the envelope of the individual chirped pulses included in the macropulse). Generally, if no macropulse shaping is used (e.g., a square-wave envelope by default), individual frequency-domain comb peaks will include side lobes from the square-shaped envelope of the macropulse.

A windowing function can be applied to the macropulse to suppress the side lobes. In an illustrative example, a Kaiser-Bessel (e.g., using a parameter, β=7) window function can be used, such as shown for pulse train 716 of FIG. 7A. For example, a first frequency-domain comb 712A can include a comb peak 714A with significant side lobes, such as corresponding to the square enveloped of the macropulse. In contrast, a second frequency-domain 714A can include a comb peak 714B with such side loves suppressed via a time-domain windowing of the macropulse.

In an example, the window function can be applied to the detected pulse train in the time-domain (in addition to, or instead of applying such a window to the stimulus pulse train). This approach can be desirable if frequency multipliers are used in the comb source since such multipliers can have limited dynamic range and thus skew the overall pulse shape when operated at high power (e.g., at or near an amplitude compression point).

Such side lobe suppression for the individual frequency-domain comb peaks can improve the baseline resolution of the frequency-domain comb, such as increasing the possible channel density that can be achieved while maintaining high inter-comb-peak isolation when bandwidth compression is used in a dual comb detection system, such as when a first comb is offset in frequency from a second comb.

FIGS. 8A-D illustrate generally illustrative examples of frequency-domain combs before and after frequency multiplication of the corresponding time-domain chirped pulse train, such as using apparatus or techniques discussed above or below, such as in the examples of FIG. 2, or other examples. When the chirped pulse train waveform is applied to a frequency multiplier, the bandwidth of the pulse is expanded by the multiplication factor of the multiplier. This can be contrasted to using square wave pulse without a frequency chirp, where the absolute bandwidth remains constant upon frequency multiplication. Any frequency shift achieved by phase shifting of each micropulse is increased by the multiplication factor of the device. However, the other comb parameters (comb peak frequency spacing and resolution) are maintained substantially unchanged.

In the illustrative examples of FIGS. 8A-D, a first frequency-domain comb 812A, such as including a first bandwidth of about 2.4 GHz and a comb peak separation, "$f_s$," of about 14.993 MHz, such as established using an AWG, can be frequency multiplied, to obtain a second frequency-domain comb 812B including a wider second bandwidth of about 5 GHz, but while still maintaining the same comb peak separation, "$f_s$." The second frequency-domain comb 812B includes more frequency-domain comb peaks, but the separation between adjacent peaks remains the same as the first frequency-domain comb 812A.

Figure 9:
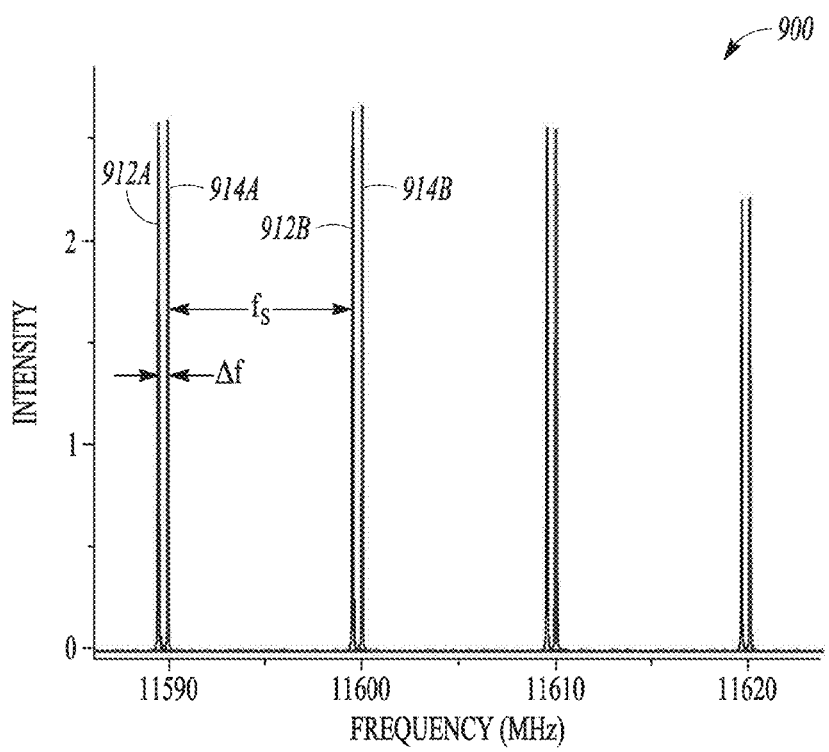
FIG. 9 illustrates generally an illustrative example of a frequency-domain comb before and after applying a phase shift to successive chirped pulses that can be included in a pulse train used to establish the frequency-domain comb.

FIG. 9 illustrates generally an illustrative example 900 of a first frequency-domain comb including first and second comb peaks 912A-B, and a second frequency-domain comb including first and second comb peaks 914A-B.

A specified time-domain offset can be applied to successive chirped pulses included in the pulse train to establish a specified frequency shift, "$\Delta f$," in the frequency-domain comb, while maintaining the same frequency separation, "$f_s$," between adjacent comb peaks. For example, a comb frequency can be shifted or stepped by applying a phase shift increasing linearly in time to successive micropulses in the macropulse train.

For spectroscopy applications, this allows the frequency to be stepped in increments smaller than the comb peak frequency spacing, "$f_s$," such as to provide full frequency coverage at a desired frequency sampling resolution. For example, a first array of frequencies including the first and second peaks 912A-B of the first frequency-domain comb can be used for a first spectroscopic measurement, in a multiplexed manner. A second array of frequencies including the first and second peaks 914A-B of the second frequency-domain comb (e.g., including linearly increasing phase shift for successive chirp pulses included in the pulse train establishing the second frequency-domain comb) can be used for a second spectroscopic measurement, such as corresponding to frequencies located between the frequency-domain comb peaks of the first frequency-domain comb.

$$\text{Chirp\_Pulse}(t, i) := \sin\left[2 \cdot \pi \cdot (\text{Chirp\_Start} \cdot 10^6) \cdot t + \right. \qquad \text{[EQN. 1]}$$
$$2 \cdot \pi \cdot [(\text{Chirp\_Stop} - \text{Chirp\_Start}) \cdot 10^6] \cdot$$
$$\left. \frac{t^2}{2 \cdot \text{Chirp\_Duration} \cdot 10^{-6}} + 2 \cdot \pi \cdot i \cdot \left(\frac{\text{Freq\_Shift}}{\text{Freq\_Spacing}}\right)\right]$$

In an illustrative example, EQN. 1 can represent an individual chirped pulse, as a function of time, "t," and an index (e.g., a sequence number), "i," of the pulse in the pulse train. In EQN. 1, "Chirp_Start," and "Chirp_Stop" can represent respectively a start and a stop frequency in MHz for the swept bandwidth of the chirped pulse, "Chirp_Duration" can represent a chirped pulse duration in microseconds, and the phase term can vary the phase of successive pulses (i=0, 1, 2 . . . ) according to a ratio of the desired frequency shift, "Freq_Shift," to the desired separation between comb peaks, "Freq_Spacing," multiplied by $2\pi$ times the sequence index.

Figure 10A:
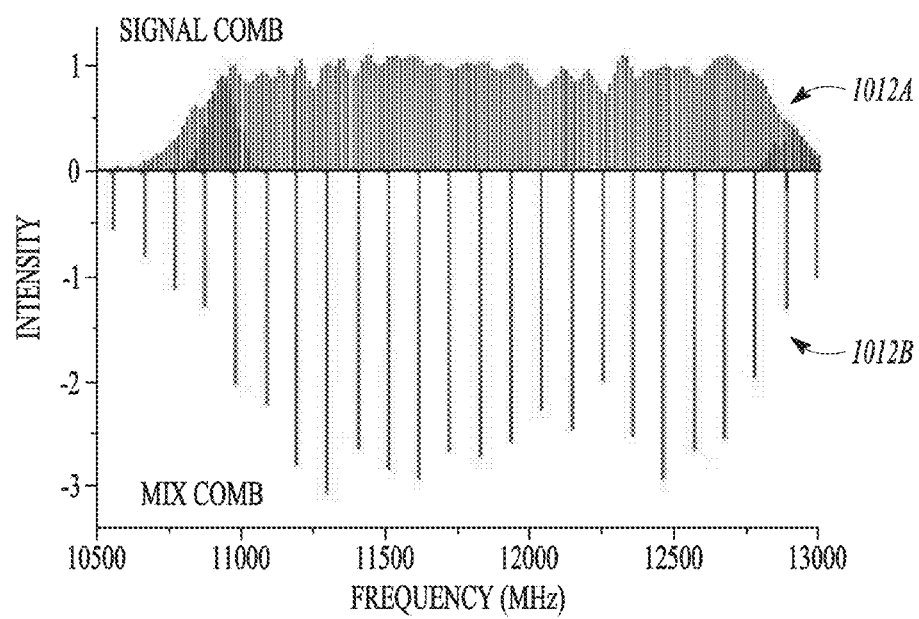
FIGS. 10A-C illustrate generally an illustrative example of downconversion of a time-domain response corresponding to a frequency-domain response comb structure, such as prior to sampling using a bandwidth-limited digitizer.
Figure 10B:
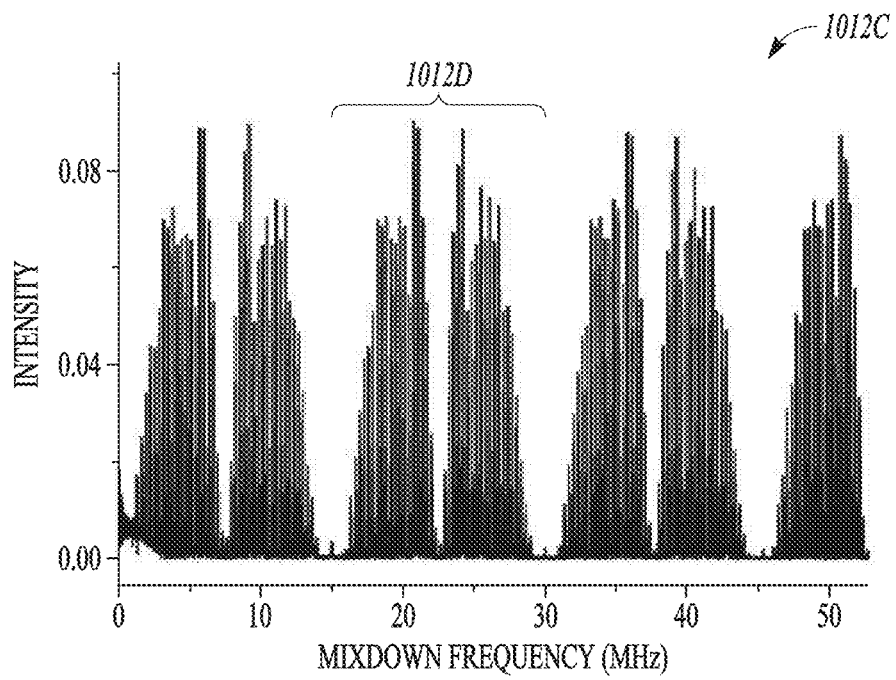
Figure 10C:
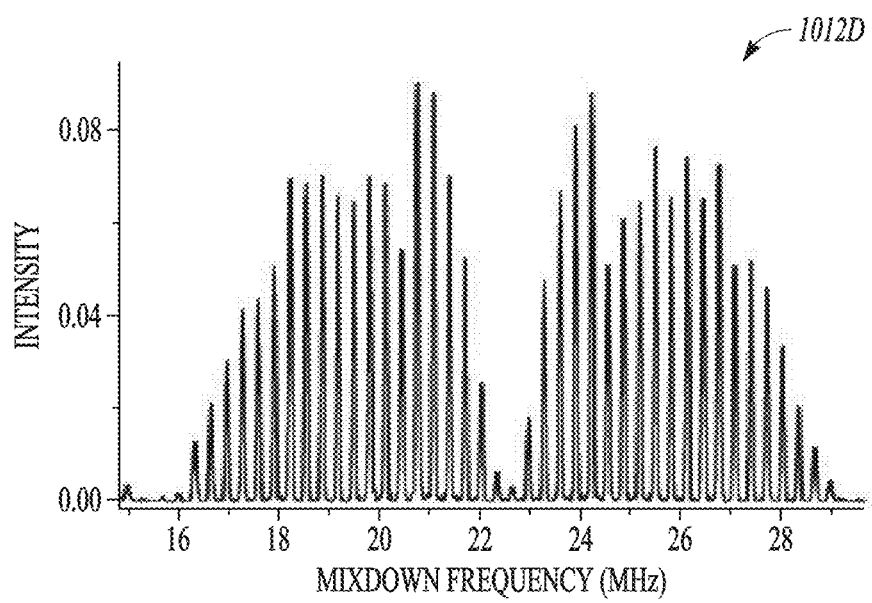

FIGS. 10A-C illustrate generally an illustrative example of downconversion of a time-domain response corresponding to a frequency-domain comb structure, such as prior to sampling using a bandwidth-limited digitizer.

A high speed digitizer can be used to detect or sample a time-domain response to chirped-pulse train stimulus (e.g., establishing a frequency-domain comb). For example, a time-domain response macropulse (e.g., pulse train) can be detected in the time-domain by using a high bandwidth digitizer (e.g., a digital oscilloscope or high-speed analog-to-digital converter, or other digitizer). Such a direct sampling approach generally includes using a digitizer having sampling rate that is at least twice the frequency of the comb peaks of interest (e.g., a Nyquist criterion). The comb spectrum can be obtained by using a discrete Fourier transform, such as a fast Fourier transformation (FFT) of the discrete information obtained by the digitizer.

Responses including frequency components outside the direct-conversion bandwidth of the detector can be acquired. In an example, the time-domain response waveform can be mixed with a single frequency phase-locked source (a phase locked dielectric resonator oscillator or other oscillator), such as to downconvert the frequency-domain comb information to a range within the usable bandwidth of the digitizer. However, this approach can still have limitations as the total bandwidth of the frequency-domain comb information must be within the Nyquist zone of the digitizer to obtain an entirety of the frequency-domain comb information. These two detection approaches (direct sampling or downconversion and sampling) can be inefficient because most of the detection bandwidth does not contain information (e.g., most of the detection bandwidth corresponds to "whitespace" between measurable comb-peaks).

The present inventors have recognized that the detection bandwidth used to detect the all frequency-domain comb information can be compressed by mixing a first time-domain response (e.g., corresponding to a first frequency-domain comb 1012A including information obtained from the sample) with a second time-domain waveform (e.g., establishing a second frequency-domain comb 1012B including a comb peak separation that is larger than the first frequency-domain comb).

Frequency comb-peak information corresponding to the first frequency-domain comb 1012A can be interleaved, and compressed into the available detection bandwidth of a digitizer. In an example, each frequency-domain comb peak can be mapped into a corresponding peak location (e.g., a detection frequency) within the detector bandwidth, so that the original broadband spectrum (e.g., the first frequency-domain comb 1012A) can be reconstructed.

The parameters of the second (e.g., more coarse) frequency-domain comb 1012B can be determined using information about the repetition frequency (comb peak spacing) of the first comb 1012A used for spectroscopy (e.g., the "signal comb), which can be represented by "$f_{rep}$," the baseline resolution desired for each comb signal channel, "$\Delta$," or the bandwidth, "$\Delta v$," of the comb spectrum, among other parameters. For interleaved mixing, the repetition frequency of the comb used in detection can be an integer multiple of signal comb frequency (e.g., $f_{rep}$) with an added offset frequency (e.g., $\Delta$) to enforce interleaving, and can be represented by ($N*f_{rep}+\Delta$). In some cases an overall shift of the mix comb frequency, "$\delta$," can be included.

A compression factor, "CF," can represent a ratio of the bandwidth of the sampled spectrum divided by the bandwidth of the digitizer that will be used to sample the spectrum. While the bandwidth of generally-available digitizers is rapidly increasing, a trade-off can still exist between bandwidth, dynamic range, and cost of the digitizer. A limit to the compression factor available, if using double sideband mixers, can be represented by $CF=f_{rep}/\Delta$. Generally, CF can be taken as the next lowest integer to a computed value of CF. The number of comb frequencies to perform the bandwidth compression can be represented by NC=(CF/2). The next highest integer value can be chosen to provide full coverage of the information included in the first frequency-domain comb 1012A.

An approximate frequency spacing, "FS," of the individual comb peaks in the detection comb can be obtained using information about the bandwidth of the signal comb spectrum (e.g., $\Delta v$) and the number of combs frequencies in the mix comb spectrum (e.g., NC), such as represented by FS=$\Delta v$/NC. The comb frequency spacing can be chosen such as using an integer multiple of the comb spacing in the signal comb (e.g., $f_{rep}$) to provide correct interleaving through mixing the two combs. The integer comb multiplier (e.g., CM) can be chosen, such as the next largest integer of the relationship CM=FS/$f_{rep}$. The comb spacing of the second frequency-domain comb 1012B that can be used for bandwidth compression in the detection can be represented by (CM*$f_{rep}$+$\Delta$), where CM can be selected as an integer value as described above. The added frequency $\Delta$ can be used to shift each detected comb over to the next clear detection channel.

In an example, the frequency-domain comb 1012A can be shifted to a desired comb starting point for an individual experiment, such as via phase shifting successive chirped pulse micropulses included in a macropulse (e.g., as shown in the example of FIG. 9). The final comb frequencies used in the detection can be represented by N*(CM*$f_{rep}$+$\Delta$)+$\delta$, where $\delta$ can represent the frequency shift added, if desired.

In an example using single sideband mixers, the techniques discussed above can be generalized. When the time-domain waveform establishing the second frequency-domain comb 1012B is mixed with the time-domain waveform establishing the first frequency-domain comb 1012A in a mixer, comb frequencies are generally mapped into a frequency range of bandwidth that can be represented by ½ (CM*$f_{rep}$+$\Delta$). Such a comb pattern repeats as frequency increases so that all of the frequency-domain combs can be individually detected by selecting any frequency range corresponding to the ½ (CM*$f_{rep}$+$\Delta$) bandwidth range.

Detection of frequency-domain information can be moved to a desired range of frequencies if there is excessive noise at low frequency or in any other range (due to co-channel interference or other sources of measurement error). The use of various different comb structures for the detection comb (e.g., the second frequency-domain comb 1012B) makes it possible to accommodate a large number of measurement configurations that can be specified for overall time resolution in the measurement (the duration of the macropulse) or for a large number of closely spaced frequency-domain combs for a high spectral resolution, or both.

As an example, a time-domain pulse train can be used to establish a frequency-domain comb covering 1 GHz of bandwidth, such as in the frequency range of 11-12 GHz, such as including a comb spacing of 10 MHz ($f_{rep}$=10 MHz). In this illustrative example, if a baseline resolution of 500 kHz is desired, the compression factor, such as using a double sideband mixer, can be CF=20. The comb spacing for the detection comb in this illustrative example is 100.5 MHz (e.g., the second frequency-domain comb 1012B). The 1 GHz frequency range of the signal comb (e.g., the first frequency-domain comb 1012A) can be compressed into a detection bandwidth of about 50.25 MHz, such as including a third, interleaved, frequency-domain comb 1012C, such as shown in FIG. 10B, including a detail region 1012D, shown in FIG. 10C.

Figure 11:
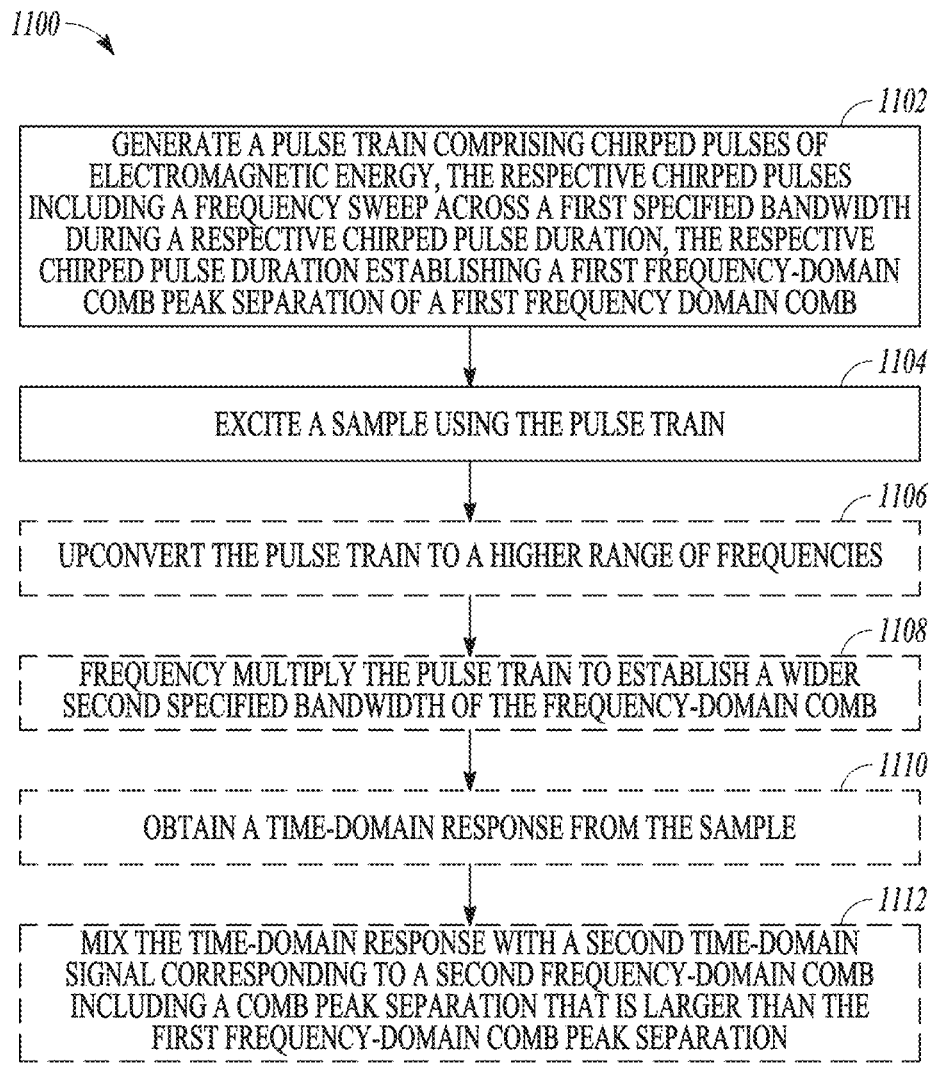
FIG. 11 illustrates generally an example that can include a technique to establish a frequency-domain comb.

FIG. 11 illustrates generally an example that can include a technique 1100 (e.g., a method or instructions to be performed by a processor such as to cause an apparatus to perform a method) to establish a frequency-domain comb. The example of FIG. 11 can include using techniques or apparatus discussed in the examples above, such as discussed in FIG. 1-2, 3A-C, 4A-C, 5A-C, 6A-C, 7A-C, 8A-D, 9, or 10A-C. At 1102, a pulse train can be generated, such as using an AWG. The pulse train can include chirped pulses of electromagnetic energy, the respective chirped pulses including a frequency sweep across a first specified bandwidth during a respective chirped pulse duration. The respective chirped pulse duration can establishing a first frequency-domain comb peak separation of a first frequency-domain comb.

In an example, at 1104, a sample can be excited (e.g., irradiated or otherwise exposed to electromagnetic energy established at 1102). One or more of absorption or emission of the sample can be monitored in response to the excitation. For example, at 1110, a time-domain response can be obtained such as corresponding to a time-domain absorption or emission signature provided by the sample. The obtained time-domain information can be transformed, such as using Fourier transform, to obtain a spectrum. The spectrum can include one or more of phase or amplitude information. For example, phase information can include information about a dispersion property of a sample.

Other techniques can be used, such as to provide a stimulus signal within a desired range of frequencies, even when such frequencies are beyond the bandwidth or frequency range of the AWG (e.g., beyond about 12 GHz, such as corresponding to an AWG configured to provide an output at 24 Gs/s.) For example, at 1106, the pulse train generated at 1102 can be upconverted to a higher range of frequencies, such as using a mixer or one or more other devices or circuits. In an example, at 1108, the pulse train generated at 1102 can be frequency multiplied to establish a wider second specified bandwidth of the frequency-domain comb.

In an example, at 1112, a time-domain response obtained from the sample (e.g., obtained at 1110), can be mixed with a second time-domain signal corresponding to a second frequency-domain comb including a comb-peak separation that is larger than the first frequency-domain comb peak separation.

Various Notes & Examples

Example 1 includes subject matter, (such as a method, a means for performing acts, or a machine readable medium including instructions, that, when performed by the machine, cause the machine to perform acts) comprising generating a pulse train comprising chirped pulses of electromagnetic energy, the respective chirped pulses including a frequency sweep across a first specified bandwidth during a respective chirped pulse duration, the respective chirped pulse duration establishing a first frequency-domain comb peak separation, and exciting a sample using the pulse train. In Example 1, a width of a frequency-domain comb peak is established at least in part by a total duration of the pulse train, and a bandwidth of a first frequency-domain comb is determined at least in part by the first specified bandwidth of the frequency sweep of the respective chirped pulses.

In Example 2, the subject matter of Example 1 can optionally include a pulse train comprising chirped pulses respectively sweeping across a first range of frequencies corresponding to the first specified bandwidth, upconverting the pulse train to a higher second range of frequencies, frequency multiplying the pulse train to establish a wider second specified bandwidth of the first frequency-domain comb, and exciting the sample using the upconverted and frequency multiplied pulse train.

In Example 3, the subject matter of one or any combination of Examples 1-2 can optionally include applying a specified time-domain window to shape one or more of the pulse train or respective chirped pulses.

In Example 4, the subject matter of one or any combination of Examples 1-3 can optionally include generating the pulse train using an arbitrary waveform generator (AWG).

In Example 5, the subject matter of one or any combination of Examples 1-4 can optionally include obtaining a time-domain response from the sample in response to the excitation of the sample, and mixing the time-domain response with a second time-domain signal corresponding to a second frequency-domain comb, the second frequency-domain comb including a comb peak separation that is larger than the first frequency-domain comb peak separation.

In Example 6, the subject matter of one or any combination of Examples 1-5 can optionally include mixing the time-domain response with a second time-domain signal including generating a bandwidth-compressed response including interleaved frequency-domain information corresponding to the time-domain response of the sample.

In Example 7, the subject matter of one or any combination of Examples 1-6 can optionally include transforming the time-domain response to obtain one or more of frequency-domain magnitude or phase information corresponding to the second, higher range of frequencies and the wider second specified bandwidth of the first frequency-domain comb.

In Example 8, the subject matter of one or any combination of Examples 1-7 can optionally include determining a characteristic of the sample using the magnitude or phase information.

In Example 9, the subject matter of one or any combination of Examples 1-8 can optionally include generating a specified time-domain phase offset to successive chirped pulses included in the pulse train to establish a specified frequency shift of the frequency-domain comb.

In Example 10, the subject matter of one or any combination of Examples 1-9 can optionally include generating a specified time-domain phase offset to establish the second frequency-domain comb, the second frequency-domain comb including comb peaks located between the locations of the frequency-domain comb peaks of the first frequency-domain comb.

Example 11 can include, or can optionally be combined with the subject matter of one or any combination of Examples 1-10 to include, subject matter (such as an apparatus) comprising a waveform generator circuit configured to generate a pulse train comprising chirped pulses of electromagnetic energy to excite a sample, the respective chirped pulses including a frequency sweep across a first specified bandwidth during a respective chirped pulse duration, the respective chirped pulse duration establishing a first frequency-domain comb peak separation, a width of a frequency-domain comb peak established at least in part by a total duration of the pulse train, and a bandwidth of a first frequency-domain comb determined at least in part by the first specified bandwidth of the respective chirped pulses.

In Example 12, the subject matter of Example 11 can optionally include a pulse train comprising chirped pulses respectively sweeping across a first range of frequencies corresponding to the first specified bandwidth, a first mixer circuit configured to upconvert the pulse train to a higher second range of frequencies, a frequency multiplier configured to multiply the frequency of the pulse train to establish a wider second specified bandwidth of the first frequency-domain comb in the higher second range of frequencies to excite the sample.

In Example 13, the subject matter of one or any combination of Examples 11-12 can optionally include a pulse train comprising a specified time-domain window to shape one or more of the pulse train or respective chirped pulses.

In Example 14, the subject matter of one or any combination of Examples 11-13 can optionally include a detector configured to obtain a time-domain response from the sample in response to the excitation of the sample.

In Example 15, the subject matter of one or any combination of Examples 11-14 can optionally include a detector configured to obtain a time-domain response from the sample in response to the excitation of the sample, and a second mixer circuit configured to mix the time-domain response with a second time-domain signal corresponding to a second frequency-domain comb, the second frequency-domain comb including a comb peak separation that is larger than the first frequency-domain comb peak separation.

In Example 16, the subject matter of one or any combination of Examples 11-15 can optionally include a second mixer circuit configured to generate a bandwidth-compressed response including interleaved frequency-domain information corresponding to the time-domain response of the sample.

In Example 17, the subject matter of one or any combination of Examples 11-16 can optionally include a signal processor circuit configured to transform the time-domain response to obtain one or more of frequency-domain magnitude or phase information corresponding to the second, higher range of frequencies and the wider second specified bandwidth of the first frequency-domain comb.

In Example 18, the subject matter of one or any combination of Examples 11-17 can optionally include a signal processor circuit configured to determine a characteristic of a sample using the magnitude or phase information.

In Example 19, the subject matter of one or any combination of Examples 11-18 can optionally include a waveform generator circuit configured to generate a specified time-domain phase offset to successive chirped pulses included in the pulse train to establish a specified frequency shift of the frequency-domain comb.

In Example 20, the subject matter of one or any combination of Examples 11-19 can optionally include a waveform generator configured to generate the specified time-domain phase offset to establish the second frequency-domain comb, the second frequency-domain comb including comb peaks located between the locations of the frequency-domain comb peaks of the first frequency-domain comb.

Example 21 can include, or can optionally be combined with the subject matter of one or any combination of Examples 1-20 to include, subject matter (such as an apparatus) comprising a means for generating a pulse train comprising chirped pulses of electromagnetic energy to excite a sample, the respective chirped pulses including a frequency sweep across a first specified bandwidth during a respective chirped pulse duration, the respective chirped pulse duration establishing a first frequency-domain comb peak separation, a width of a frequency-domain comb peak established at least in part by a total duration of the pulse train, a bandwidth of a first frequency-domain comb determined at least in part by the first specified bandwidth of the frequency sweep of the respective chirped pulses.

In Example 22, the subject matter of Example 21 can optionally include a pulse train comprising chirped pulses respectively sweeping across a first range of frequencies corresponding to the first specified bandwidth, a means for upconverting the pulse train to a higher second range of frequencies, and a means to multiply the frequency of the pulse train to establish a wider second specified bandwidth of the first frequency-domain comb in the higher second range of frequencies to excite the sample.

In Example 23, the subject matter of one or any combination of Examples 21-22 can optionally include a means for obtaining a time-domain response of the sample, a means for providing a bandwidth-compressed response including interleaved frequency-domain information corresponding to the time-domain response of the sample.

Example 24 can include, or can optionally be combined with any portion or combination of any portions of any one or more of Examples 1-23 to include, subject matter that can include means for performing any one or more of the functions of Examples 1-23, or a machine-readable medium including instructions that, when performed by a machine, cause the machine to perform any one or more of the functions of Examples 1-23.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method, comprising:
generating a pulse train comprising phase-coherent frequency-chirped pulses of at least one of microwave, millimeter-wave, or sub-millimeter wave electromagnetic energy;
applying a time-domain window to at least one frequency-chirped pulse in the pulse train; and
exciting a sample using the pulse train.

2. The method of claim 1, the pulse train including at least one frequency-chirped pulse within a frequency range of about 1 GHz to about 1 THz.

3. The method of claim 1, the pulse train including at least one frequency-chirped pulse within a frequency range of about 3 THz to about 30 THz.

4. The method of claim 1, wherein the pulse train includes unevenly spaced frequency-domain components.

5. The method of claim 1, wherein the pulse train includes evenly spaced frequency-domain components.

6. The method of claim 1, further comprising applying a phase shift to each frequency-chirped pulse in the pulse train, the phase shift applied to a later pulse of the pulse train being greater than the phase shift applied to an earlier pulse of the pulse train.

7. The method of claim 1, the generating the pulse train including, for each frequency-chirped pulse of the pulse train:
generating a baseband frequency-chirped pulse;
upconverting the baseband frequency-chirped pulse to generate an upconverted frequency-chirped pulse; and
frequency multiplying the upconverted frequency-chirped pulse to produce the frequency-chirped pulse.

8. The method of claim 1, wherein the pulse train is a first pulse train of a plurality of pulse trains, and wherein the phase-coherent frequency-chirped pulses in the first pulse train of the plurality of pulse trains have the same phase as phase-coherent frequency-chirped pulses in at least one other pulse train of the plurality of pulse trains.

9. The method of claim 1, further comprising:
detecting, from the sample and in response to the excitation, a sample response; and
applying a pulse-shaping window to the sample response.

10. The method of claim 1, the pulse train having a first comb peak separation, the method further comprising:
detecting, from the sample and in response to the excitation, a sample response; and
mixing the sample response with a frequency domain comb, the frequency domain comb having a second comb peak separation that is greater than the first comb peak separation.

11. An apparatus, comprising:
a signal generator configured to:
generate a pulse train comprising phase-coherent frequency-chirped pulses of at least one of microwave, millimeter-wave, or sub-millimeter wave electromagnetic energy; and
apply a time-domain window to at least one frequency-chirped pulse in the pulse train; and
an antenna operably coupled to the signal generator and configured to couple the pulse train to a sample, the pulse train exciting the sample.

12. The apparatus of claim 11, the pulse train including at least one frequency-chirped pulse within a frequency range of about 1 GHz to about 1 THz.

13. The apparatus of claim 11, wherein the pulse train includes unevenly spaced frequency-domain components.

14. The apparatus of claim 11, wherein the pulse train includes evenly spaced frequency-domain components.

15. The apparatus of claim 11, wherein the pulse train is a first pulse train of a plurality of pulse trains, and wherein the phase-coherent frequency-chirped pulses in the first pulse train of the plurality of pulse trains have the same phase as the phase-coherent frequency-chirped pulses in at least one other pulse train of the plurality of pulse trains.

16. The apparatus of claim 11, further comprising a sample region configured to hold the sample, the sample region coupled to the antenna.

17. The apparatus of claim 11, the signal generator including:
a waveform generator configured to generate the pulse train; and
a mixer operably coupled to the waveform generator and configured to apply the time domain window to at least one frequency-chirped pulse in the pulse train.

18. An apparatus, comprising:
a signal generator configured to:
  generate a pulse train comprising phase-coherent frequency-chirped pulses of at least one of microwave, millimeter-wave, or sub-millimeter wave electromagnetic energy; and
  apply a time-domain window to at least one chirped pulse in the pulse train; and
a waveguide operably coupled to the signal generator and configured to couple the pulse train to a sample, the pulse train exciting the sample.

19. The apparatus of claim 18, the pulse train including at least one frequency-chirped pulse within a frequency range of about 1 GHz to about 1 THz.

20. The apparatus of claim 18, wherein the pulse train includes unevenly spaced frequency-domain components.

21. The apparatus of claim 18, wherein the pulse train includes evenly spaced frequency-domain components.

22. The apparatus of claim 18, wherein the pulse train is a first pulse train of a plurality of pulse trains, and wherein the phase-coherent frequency-chirped pulses in the first pulse train of the plurality of pulse trains have the same phase as the phase-coherent frequency-chirped pulses in at least one other pulse train of the plurality of pulse trains.

23. The apparatus of claim 18, further comprising a sample region configured to hold the sample, the sample region coupled to the waveguide.

24. The apparatus of claim 18, the signal generator including:
a waveform generator configured to generate the pulse train; and
a mixer operably coupled to the waveform generator and configured to apply the time domain window to at least one frequency-chirped pulse in the pulse train.

25. A method, comprising:
generating a pulse train comprising phase-coherent frequency-chirped pulses of at least one of microwave, millimeter-wave, or sub-millimeter wave electromagnetic energy;
exciting a sample using the pulse train;
detecting, from the sample and in response to the excitation, a sample response; and
applying a pulse-shaping window to the sample response.

26. The method of claim 25, further comprising applying a phase shift to each frequency-chirped pulse in the pulse train, the phase shift associated with a later pulse of the pulse train being greater than the phase shift associated with an earlier pulse of the pulse train.

27. The method of claim 25, the generating the pulse train including, for each frequency-chirped pulse of the pulse train:
generating a baseband frequency-chirped pulse;
upconverting the baseband frequency-chirped pulse to generate an upconverted frequency-chirped pulse; and
frequency multiplying the upconverted frequency-chirped pulse to produce the at least one frequency-chirped pulse in the pulse train.

28. The method of claim 25, wherein the pulse train is a first pulse train of a plurality of pulse trains, and wherein the phase-coherent frequency-chirped pulses in the first pulse train of the plurality of pulse trains have the same phase as the phase-coherent frequency-chirped pulses in at least one other pulse train of the plurality of pulse trains.

29. The method of claim 25, the pulse train having a first comb peak separation, the method further comprising mixing the sample response with a frequency domain comb, the frequency domain comb having a second comb peak separation that is greater than the first comb peak separation.

30. The method of claim 25, wherein the applying the pulse-shaping window includes applying a window function to the sample response.

31. The method of claim 30, wherein the window function comprises a Kaiser-Bessel window function or a tapered cosine window function.

* * * * *